(12) United States Patent
Inman

(10) Patent No.: US 8,062,031 B2
(45) Date of Patent: *Nov. 22, 2011

(54) ORTHODONTIC APPLIANCE AND METHOD

(76) Inventor: Donal P. Inman, Coral Springs, FL (US)

( * ) Notice: Subject to any disclaimer, the term of this patent is extended or adjusted under 35 U.S.C. 154(b) by 176 days.

This patent is subject to a terminal disclaimer.

(21) Appl. No.: 10/915,231

(22) Filed: Aug. 10, 2004

(65) Prior Publication Data

US 2005/0069834 A1 Mar. 31, 2005

Related U.S. Application Data

(60) Provisional application No. 60/494,161, filed on Aug. 11, 2003.

(51) Int. Cl.
*A61C 3/00* (2006.01)

(52) U.S. Cl. .......................................................... 433/18

(58) Field of Classification Search ................ 433/7, 18, 433/21, 6, 19, 23–24
See application file for complete search history.

(56) References Cited

U.S. PATENT DOCUMENTS

| | | | |
|---|---|---|---|
| 1,130,242 A * | 3/1915 | Bacon | 433/21 |
| 1,139,170 A * | 5/1915 | Drissler | 433/21 |
| 1,142,467 A * | 6/1915 | Walker | 433/21 |
| 4,026,023 A * | 5/1977 | Fisher | 433/7 |
| 4,723,910 A * | 2/1988 | Keller | 433/7 |
| 4,752,222 A * | 6/1988 | Bass | 433/7 |
| 4,976,614 A * | 12/1990 | Tepper | 433/18 |
| 5,007,828 A * | 4/1991 | Rosenberg | 433/18 |
| 5,017,133 A * | 5/1991 | Miura | 433/20 |
| 5,087,196 A * | 2/1992 | Polanco | 433/21 |
| 5,096,416 A * | 3/1992 | Hulsink | 433/6 |
| 5,167,499 A * | 12/1992 | Arndt et al. | 433/7 |
| 5,829,970 A * | 11/1998 | Yousefian | 433/7 |
| 5,895,217 A * | 4/1999 | Kooiman | 433/7 |
| 6,435,871 B1 * | 8/2002 | Inman | 433/7 |
| 6,626,665 B1 * | 9/2003 | Keles | 433/18 |
| 2002/0025501 A1 * | 2/2002 | Clark | 433/18 |
| 2003/0091952 A1 * | 5/2003 | Bowman et al. | 433/18 |
| 2004/0110108 A1 * | 6/2004 | Weissbach Otte | 433/18 |

* cited by examiner

*Primary Examiner* — Cris L Rodriguez
*Assistant Examiner* — Heidi M Eide
(74) *Attorney, Agent, or Firm* — Hodgson Russ LLP

(57) ABSTRACT

An orthodontic appliance including labial and lingual bodies having teeth-contacting surfaces for acting against targeted anterior teeth of a patient and associated labial and lingual components incorporating spring-loaded biasing means for causing the labial and lingual bodies to act in generally opposed directions and in unison against the surfaces of the targeted anterior teeth. Bands for attaching the appliance to molars and a lingual support component also are provided. The foregoing is applied to a fixed spring aligner, a habit appliance and a bonded crossbite appliance, as well as appliances having new and improved labial and lingual components. The habit appliance includes a labial component to pull anterior teeth into an ideal position, and the aligner and crossbite appliances include labial and lingual components for applying corrective forces to the respective labial and lingual surfaces of the anterior teeth.

14 Claims, 30 Drawing Sheets

ORTHODONTIC APPLIANCE AND METHOD

CROSS REFERENCE TO A RELATED APPLICATION

Applicant claims priority based on U.S. provisional patent application No. 60/494,161 filed Aug. 11, 2003 and entitled "Orthodontic Appliance and Method" which is incorporated herein by reference.

BACKGROUND OF THE INVENTION

1. Field of the Invention

The present invention relates generally to orthodontic appliances and treatments, and more particularly to appliances and treatments for correction of problems specific to the anterior teeth.

2. Description of the Prior Art

Orthodontists and dental researchers are constantly searching for new and improved appliances and associated treatments for correcting problems related to the anterior teeth, including, for example, crossbites, overcrowding, rotated teeth, and splayed or flared teeth. Some prior art orthodontic appliances for treating such problems include both labial and lingual components for applying corrective forces to the respective labial and lingual surfaces of the anterior teeth identified for treatment. Although many such prior art devices are effective for accomplishing the desired correction, they leave much room for improvement.

In particular, prior art appliances which incorporate fixed, generally immovable labial and lingual components have significant disadvantages and limitations. A principal drawback is that the desired force of the labial and lingual components against the teeth steadily decreases as teeth are repositioned in response to the force. Consequently, adjustments of such prior art appliances by orthodontists or technicians are required at relatively short time intervals, requiring frequent patient visits. Furthermore, the overall treatment time is increased due to the inability to maintain a constant desired force against the teeth between adjustments.

The foregoing disadvantages, limitations and drawbacks of such prior art appliances having fixed, generally immovable labial and lingual components are avoided by the orthodontic appliance shown and described in U.S. Pat. No. 6,435,871 issued Aug. 20, 2002 the disclosure of which is hereby incorporated by reference. The appliance of that patent incorporates labial and lingual components acting in generally opposed directions, and in unison, against the respective labial and lingual surfaces of a set of targeted anterior teeth, thereby enabling the application of a relatively continuous force against the targeted teeth between scheduled treatments, with minimal reduction in applied force. This is accomplished by the labial and lingual components incorporating spring-loaded biasing means having improved flexibility. Such flexibility, in turn, enables adjustments to the appliance to be made without requiring bending or manipulation of the labial and lingual wires.

SUMMARY OF THE INVENTION

It would be highly desirable to extend the advantages of the appliance of the foregoing patent to orthodontic appliances of additional types and configurations. These would include, for example, a fixed spring aligner, a habit appliance and a bonded crossbite appliance, as well as appliances having new and improved labial and lingual components. The habit appliance includes a labial component to pull anterior teeth into an ideal position, and the aligner and crossbite appliances include labial and lingual components for applying corrective forces to the respective labial and lingual surfaces of the anterior teeth.

The following detailed description, when read in conjunction with the accompanying drawing, is in such full, clear, concise and exact terms as to enable any person skilled in the art to which it pertains, or with which it is most nearly connected, to make and use the invention.

DETAILED DESCRIPTION OF THE INVENTION

The orthodontic appliance disclosed in the afore-mentioned U.S. Pat. No. 6,435,871 includes labial and lingual bodies having teeth-contacting surfaces for acting against targeted anterior teeth of a patient and associated labial and lingual components incorporating spring-loaded biasing means for causing the labial and lingual bodies to act in generally opposed directions and in unison against the surfaces of the targeted anterior teeth.

FIGS. 1-4 show a fixed spring aligner orthodontic appliance 10 according to this invention which includes the foregoing components of the appliance of U.S. Pat. No. 6,435,871 plus bands 12 for attaching to the molars to band or fix the appliance 10 in place and a lingual support component or wire 14. The appliance 10 is used to correct anterior rotations and crowding associated with Adult Response. This appliance functions the same as the appliance of U.S. Pat. No. 6,435,871 but is banded or fixed in place so that it cannot be removed by the patient. Support wire 14 enhances the strength of the appliance framework.

Figure 1:
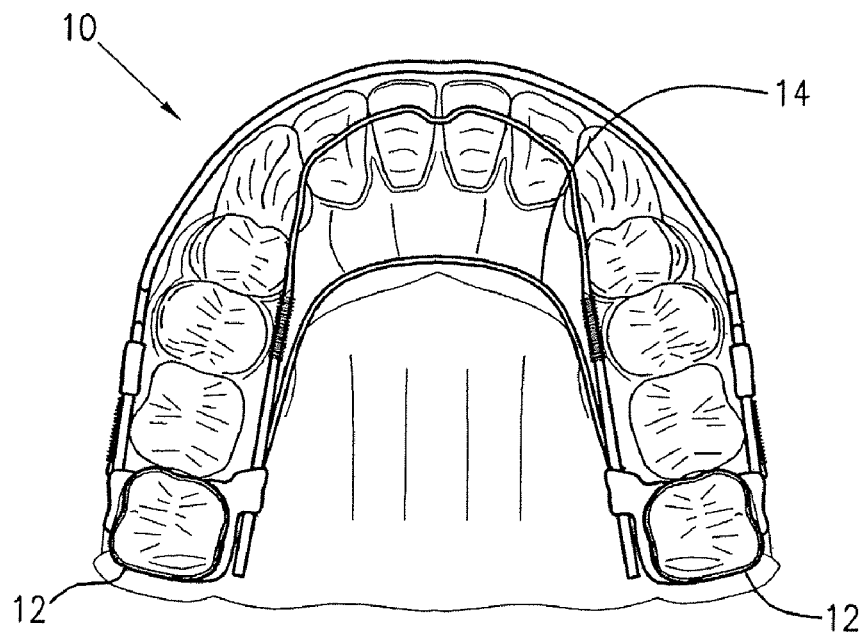
FIGS. 1-4 are perspective views of a fixed spring aligner orthodontic appliance according to this invention.
Figure 2:
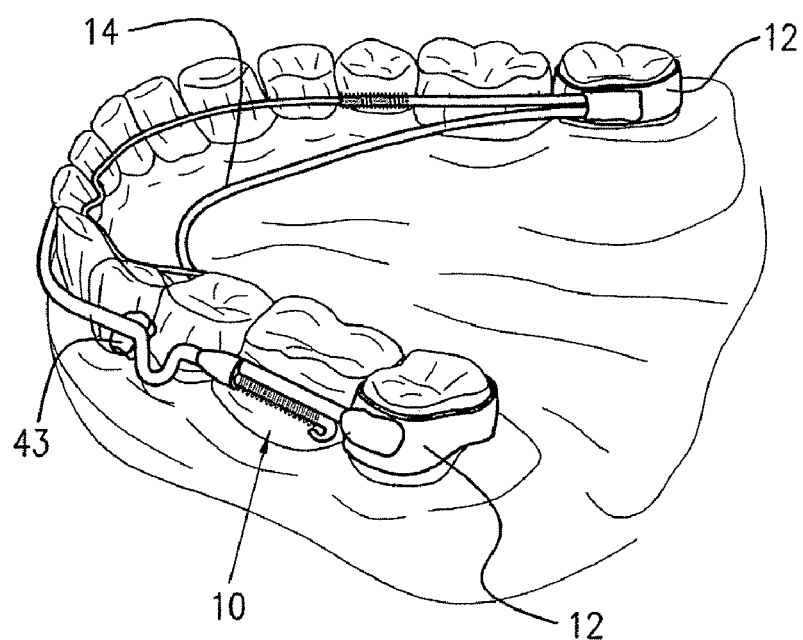
Figure 3:
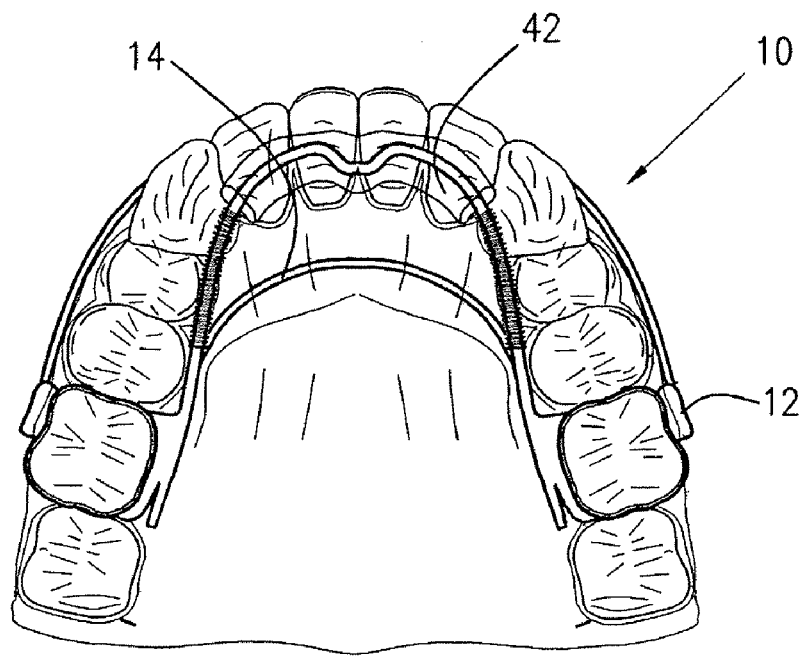
Figure 4:
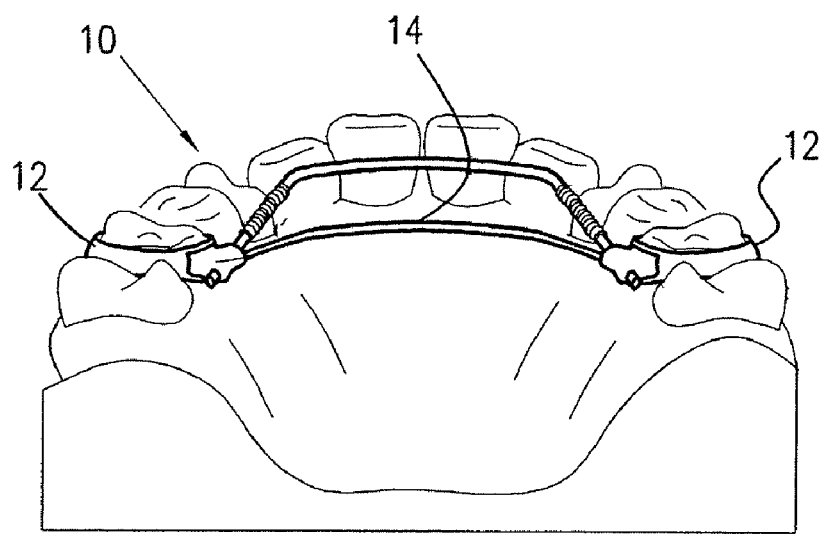
Figure 5:
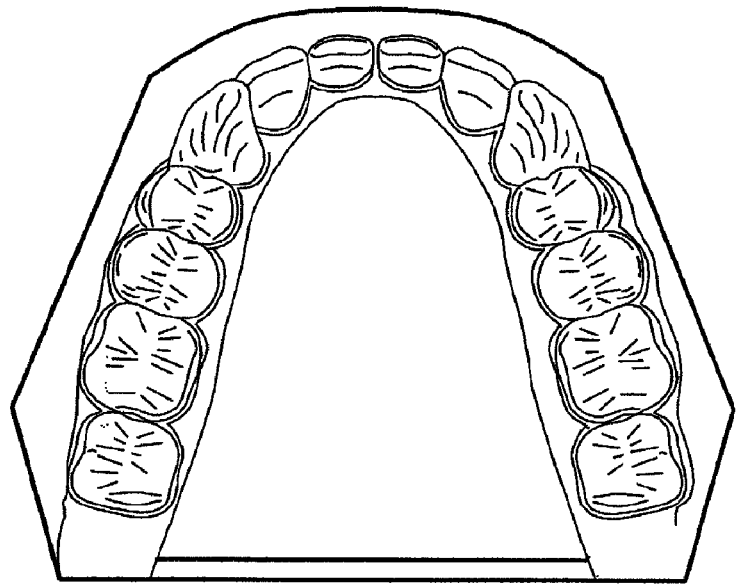
FIGS. 5-27 are perspective views illustrating a method of fabricating the appliance of FIGS. 1-4.
Figure 6:
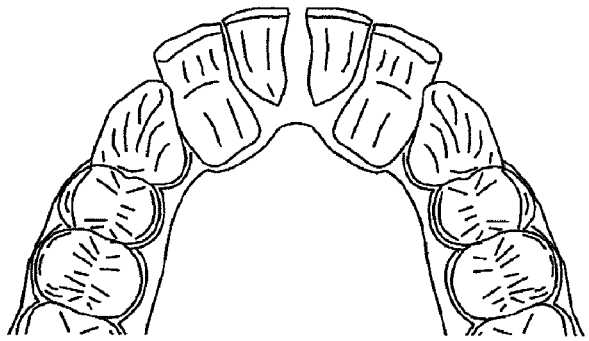
Figure 7:
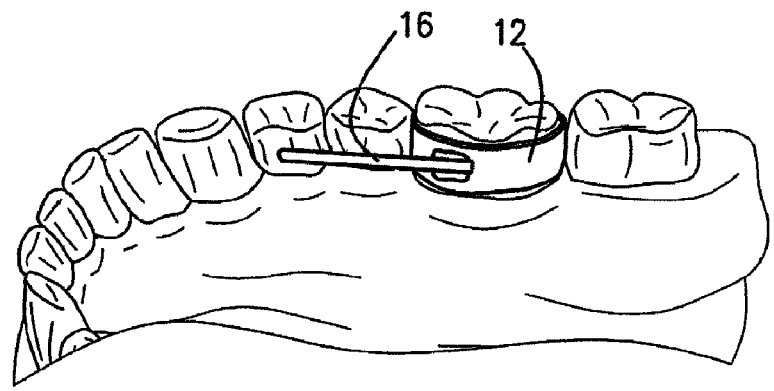
Figure 8:
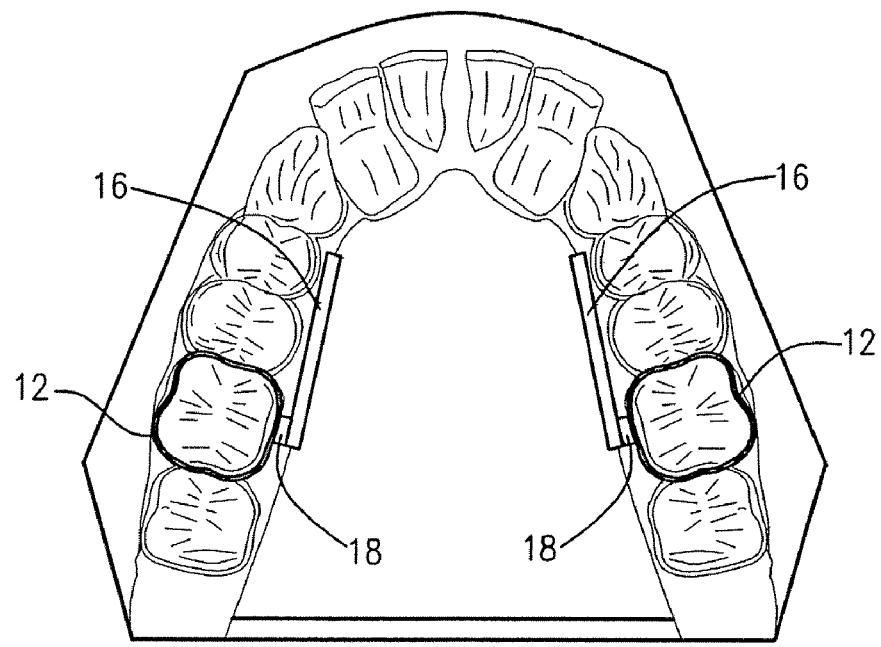

A method of fabricating appliance 10 of FIGS. 1-4 is illustrated in FIGS. 5-27. FIG. 5 represents model preparation, both original and duplicate, and FIG. 6 shows resetting maxillary/mandibular teeth on the original model. The bands 12 are shown in FIGS. 7 and 8 installed on the model teeth, in the present illustration on the first molars. A pair of 0.040 inch diameter stainless steel tubes 16 are provided, each cut to a length extending from the middle of the corresponding molar band 12 to the middle of the first bicuspid. A 4-5 mm. length of 0.028 inch diameter stainless steel wire 18 is spotwelded to the distal side of each tube 16 to set the tube lingually. Then each tube 16 and wire 18 combination is tackwelded to the occlusal-middle third of the corresponding band 12, and oriented so that each tube 16 is angled toward the gingival margin. Thus, each tube 16 is open at the molar band 12 and has a slight gingival angulation toward the anterior part of the tube.

Figure 9:
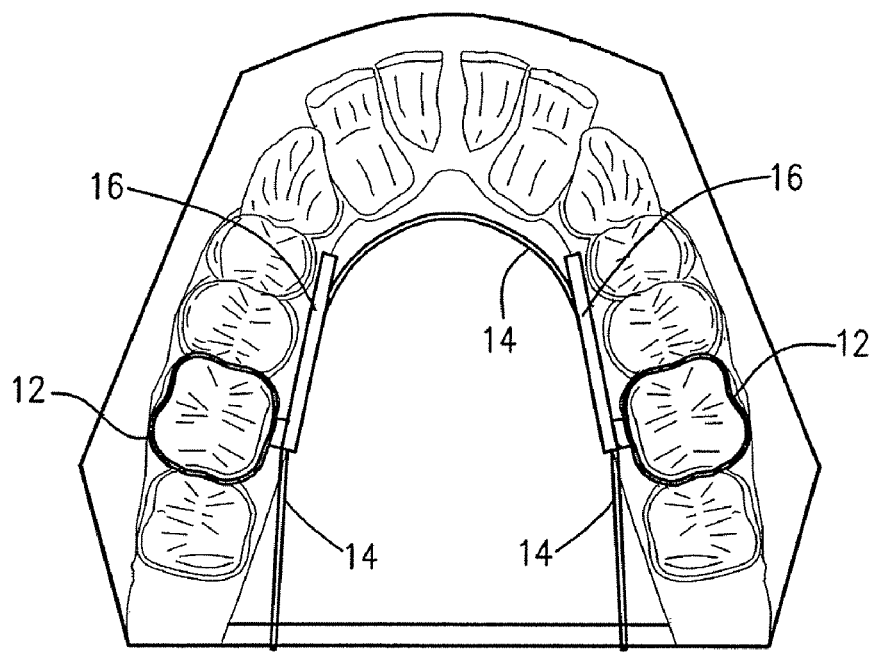
Figure 10:
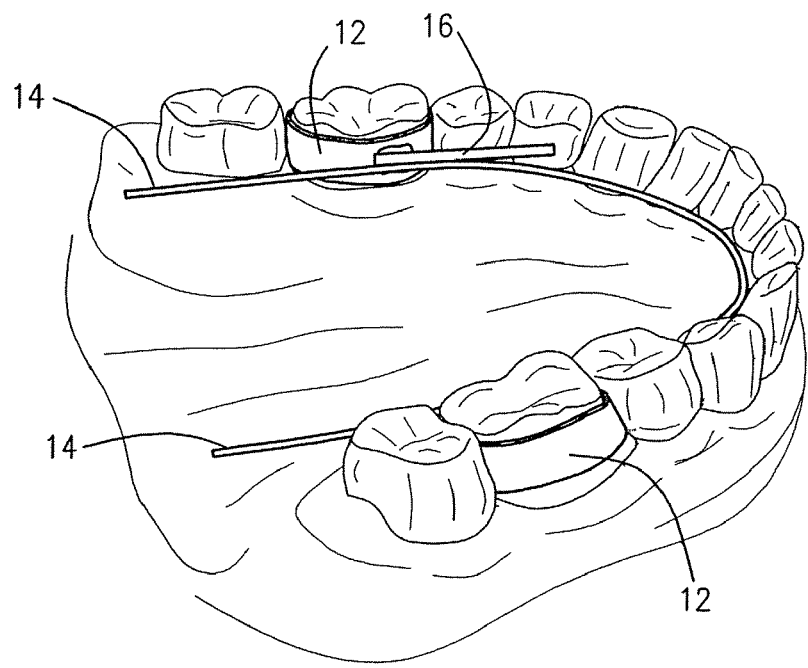
Figure 11:
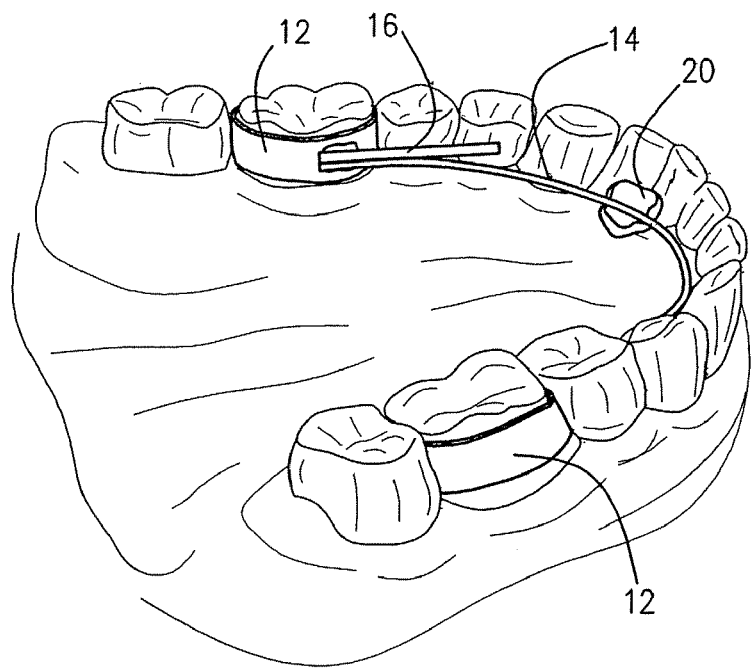
Figure 12:
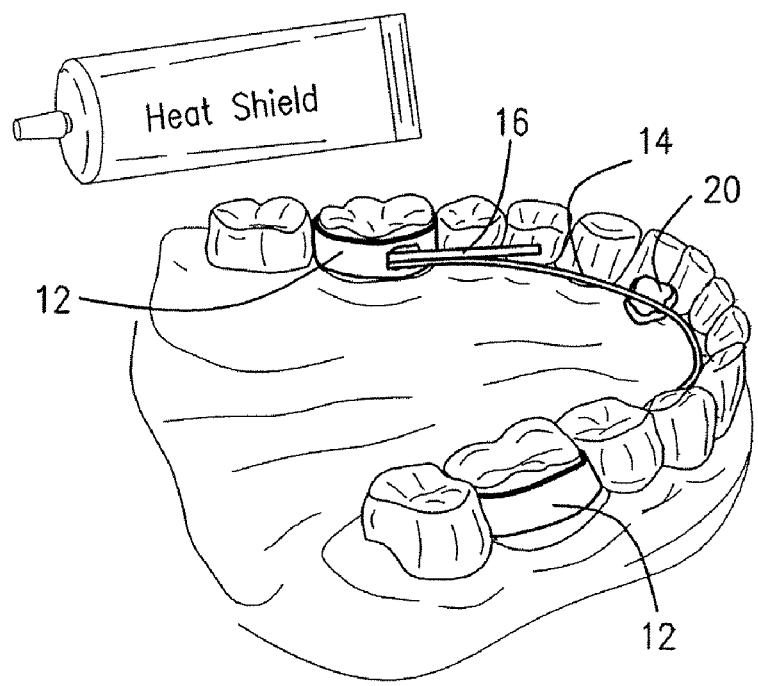
Figure 13:
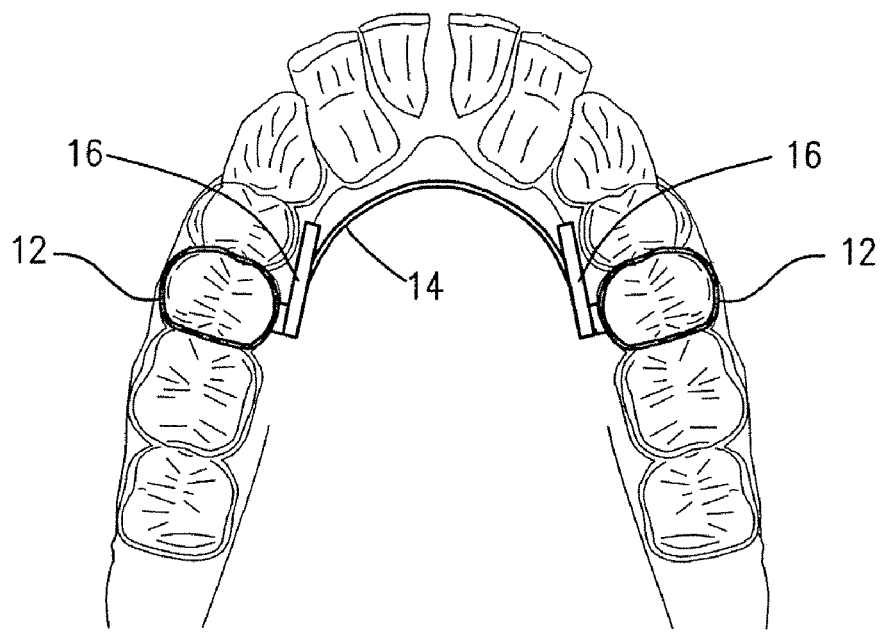

The lingual support wire 14 is shown in FIGS. 9-13. It preferably is in the form of a 7 inch length of 0.051 inch diameter stainless steel wire, and is bent under the lingual tubes 16 as shown in FIGS. 9 and 10. The wire 14 is spaced so as to be about 1.5-2 mm. away from tissue and is sloped downward to a 3-4 mm. area below the gingival margin along the anterior teeth. FIG. 11 shows the support wire 14 cut at the midpoint of each band 12, stabilized by a body 20 of MORTITE (a caulking compound) and tackwelded to the bands 12. Heat Shield is applied into the distal ends of the lingual tubes 16 as shown in FIG. 12, and the lingual metal parts, i.e. support wire 14 and tubes 16, are soldered to the bands 12 as shown in FIG. 13.

Figure 14:
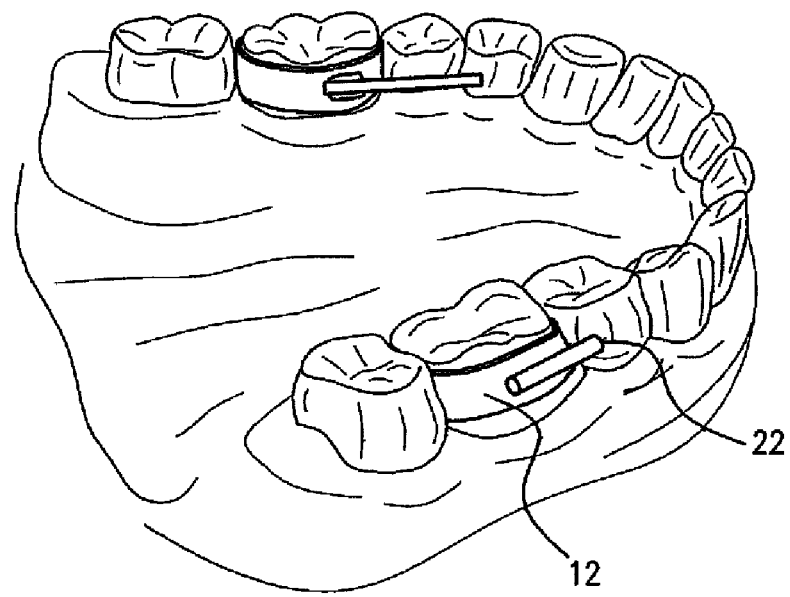
Figure 15:
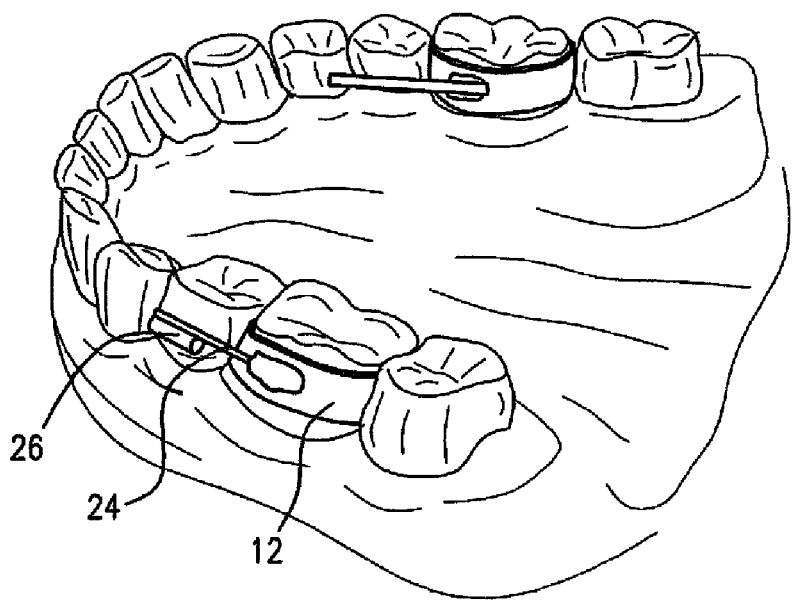
Figure 16A:
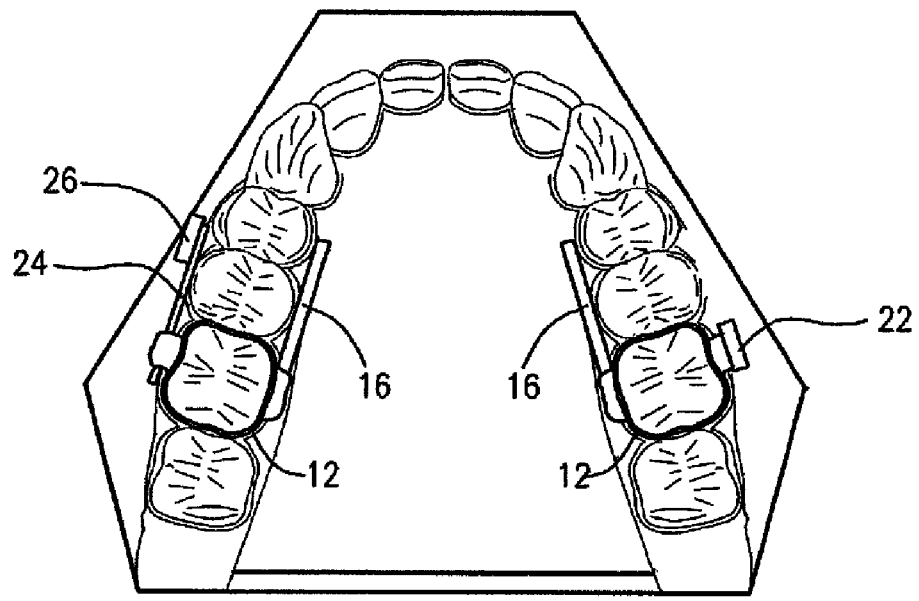
Figure 16B:
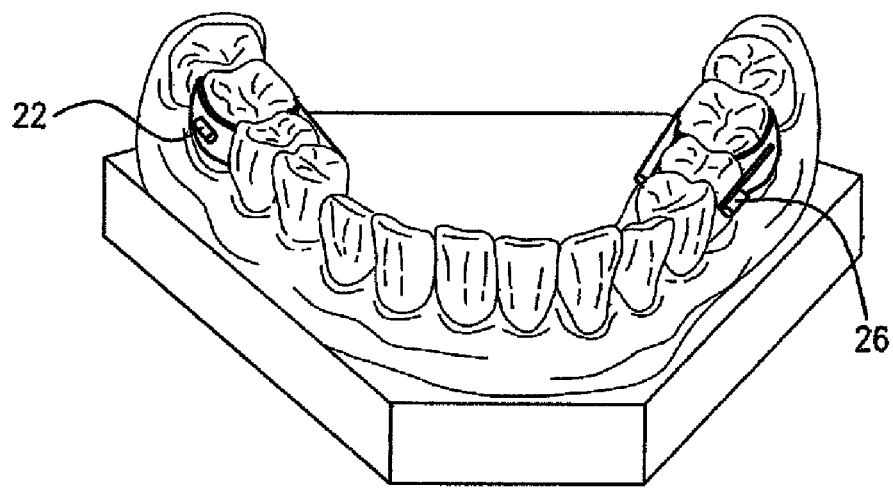

FIGS. 14-16b show alternative arrangements for providing labial wire support tubes on the outer surfaces of bands 12. A standard design is shown in FIG. 14 wherein a 0.040 inch diameter stainless steel tube 22 is tackwelded and soldered on the mesial-buccal, mid-height of a molar band 12. In the optional design of FIG. 15, a 0.036 inch diameter stainless steel cantilever arm 24 is tackwelded and soldered on the mesial-buccal, mid-height of a molar band 12. Wire aim 24 is cut near the first bicuspid. Then a 0.040 diameter stainless steel tube 26 is tackwelded and soldered to the gingival side of the anterior end of the cantilever arm 24. As shown in FIGS. 16a and 16b, the lingual tubes 16 and the labial wire support tubes 22 and 26 are disposed so as to be aligned with the dental arch form and as parallel with each other as possible.

Figure 17A:
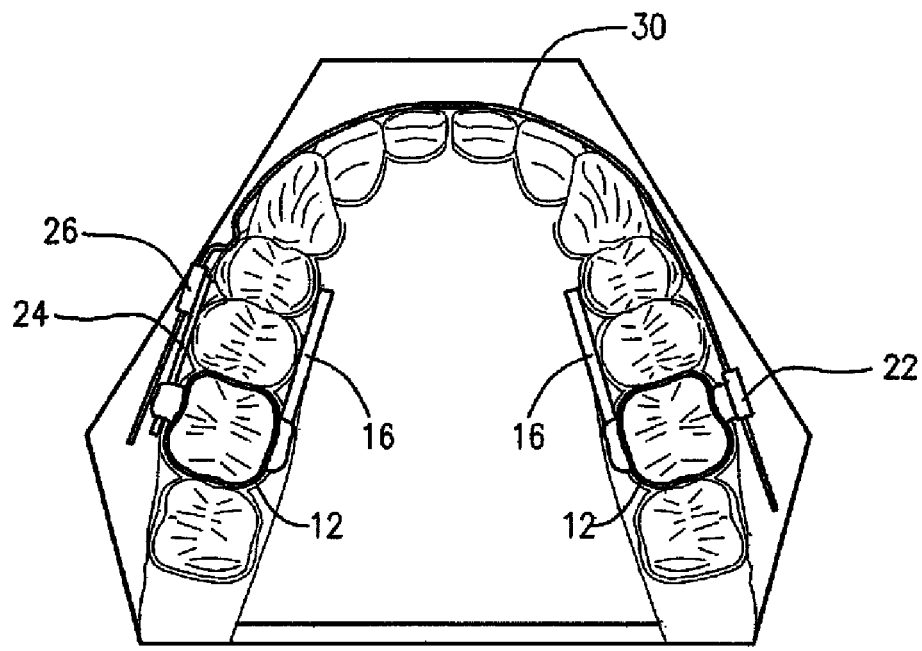
Figure 17B:
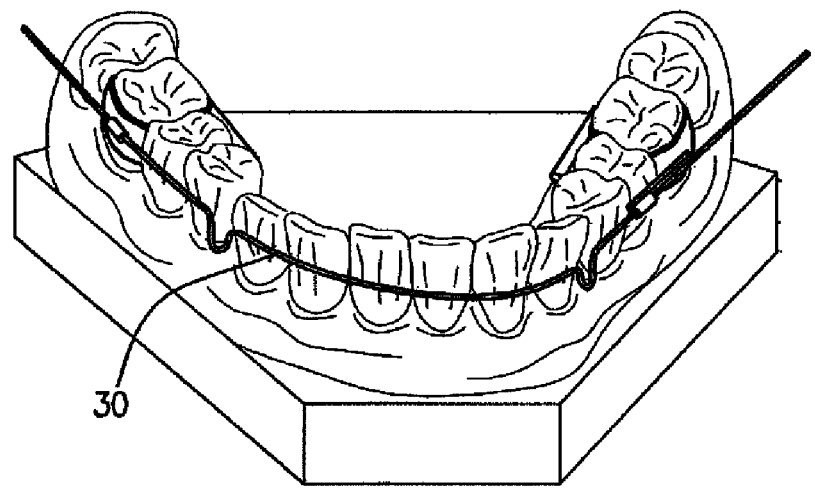

FIGS. 17a and 17b illustrate installation of the labial frame or bow wire 30. It is in the form of a 0.028 diameter yellow DURALOY wire bent to extend through both buccal tubes 22 and 26, and labial bow wire 30 is soldered on the facial surface of the first permanent molar bands 12. An offset-stop bend is placed in the wire mesial to the tube. Acrylic on labial wire 30 covers 2×2 or 3×3, based on teeth reset. A 5×7 mm. long adjustment loop is placed at the mesial third of cuspids if there is only 2×2 or less teeth reset. An adjustment loop is placed at the distal third of cuspids if they are reset.

Figure 18:
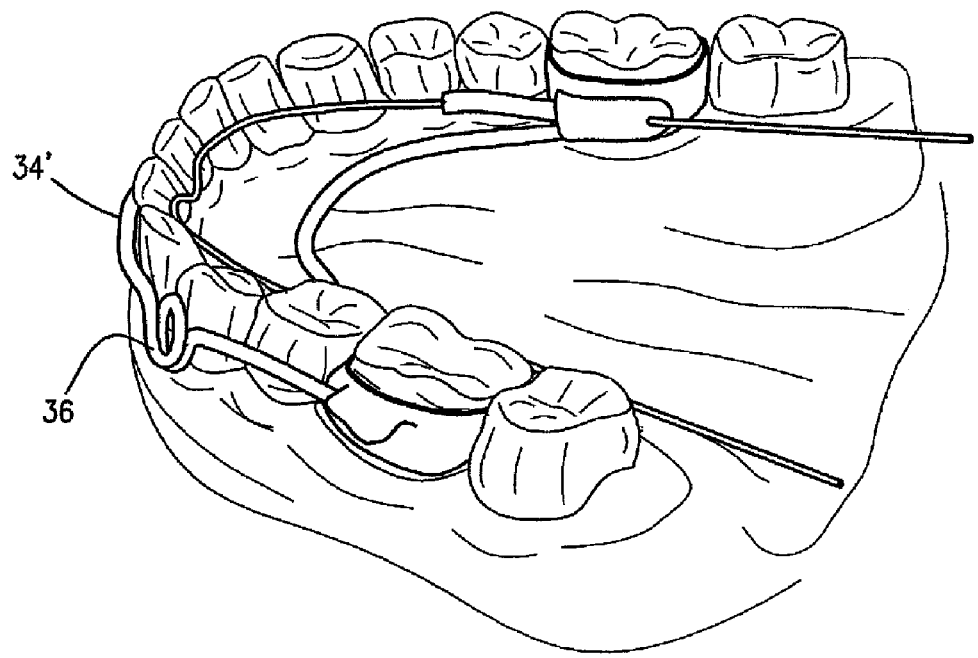

An optional form of labial bow wire 34' is shown in FIG. 18. It is fabricated using 0.030 inch diameter yellow DURALOY wire. A 5-7 mm. long adjustment loop 36 is placed at the mesial third of cuspids if there is only 2×2 or less tooth reset. The adjustment loop is placed at distal third of cuspids if they are reset. The bow 34' is placed at middle height of teeth, extends to the middle third of bands 12 and is tackwelded and soldered to the bands.

Figure 19:
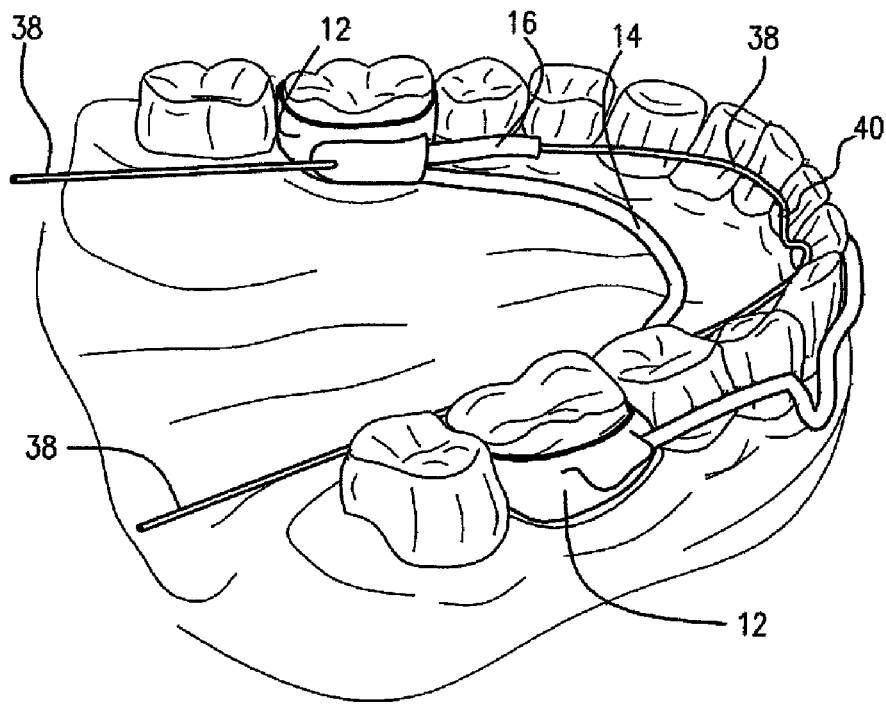

A lingual frame component 38 is shown in FIG. 19 and comprises a 0.028 inch diameter yellow DURALOY wire that is bent so as to be rounded along the lingual surface of anterior teeth and extends straight through the distal open ends of the lingual support tubes 16. The wire 38 should engage each tube 16 as straight as possible and extend through the distal ends. A "V" shaped midline bend 40 is incorporated prior to rounding the wire along the cervical/middle third height of the anterior teeth. The wire distal extension is looped to lock lingual component 38 in the tubes 16. A relief between cuspids and lingual wire 38 allows for open coil springs to be added later. Anterior acrylic 42 forming a lingual body with tooth-contacting surfaces is placed 2×2, or 3×3 if cuspids are repositioned. A tieback hole can be provided in the lingual acrylic for passive insertion.

Figure 20:
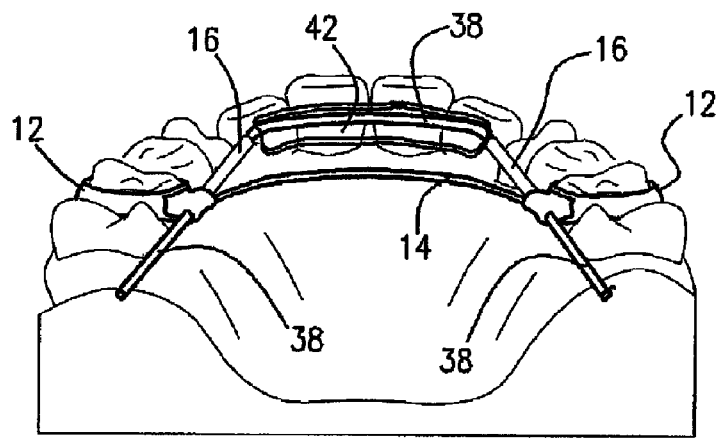
Figure 21:
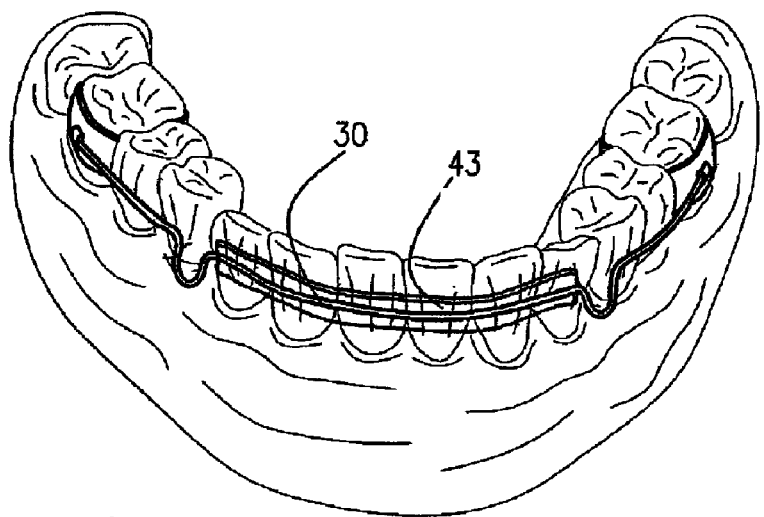
Figure 22:
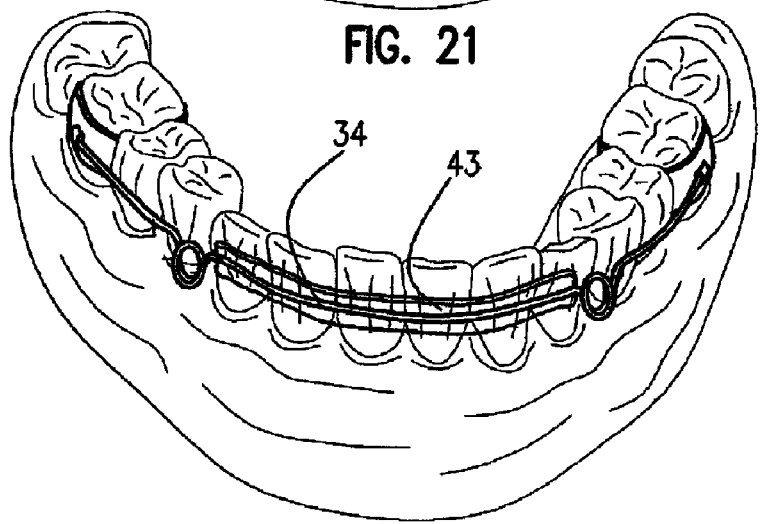

FIG. 20 illustrates the steps in fabrication wherein the model is separated and acrylic 42 is applied to lingual component 38 along the incisors (2×2), the acrylic being extended to the cuspids if reset, and the cured acrylic then is trimmed to a 4-5 mm. height with lingual wire 38 in the center, the acrylic being allowed to extend to the distal edge of the lateral incisors (or cuspids, if reset). Finally, a small tieback hole is drilled through the middle of the acrylic pad near the dental midline. As shown in FIGS. 21 and 22, for the two forms of labial bow 30 and 34, respectively, the model is separated and acrylic 43 forming a labial body having tooth-contacting surfaces is applied to the labial bow within the adjustment loops. The curved acrylic is trimmed to a height of 3-4 mm. with the bow wire in the center.

By way of example, one method of forming the lingual and labial bodies 42 and 43, respectively, can include placing a sheet of thermoplastic material over the dental model of the anterior teeth in desired position and then placing the model with plastic sheet thereover in the receptacle of a dental appliance forming machine (not shown) such as the one commercially designated Biostar® and available from Great Lakes Orthodontics Ltd., Tonawanda, N.Y. After thermal shaping by the machine and upon cooling the material is trimmed to the desired configuration. For a more detailed description of the Biostar® machine and its method of operation, reference may be made to U.S. Pat. No. 3,768,164 issued Oct. 30, 1973 and entitled "Method Of Making A Dental Appliance", the disclosure of which is incorporated herein by reference.

Figure 23:
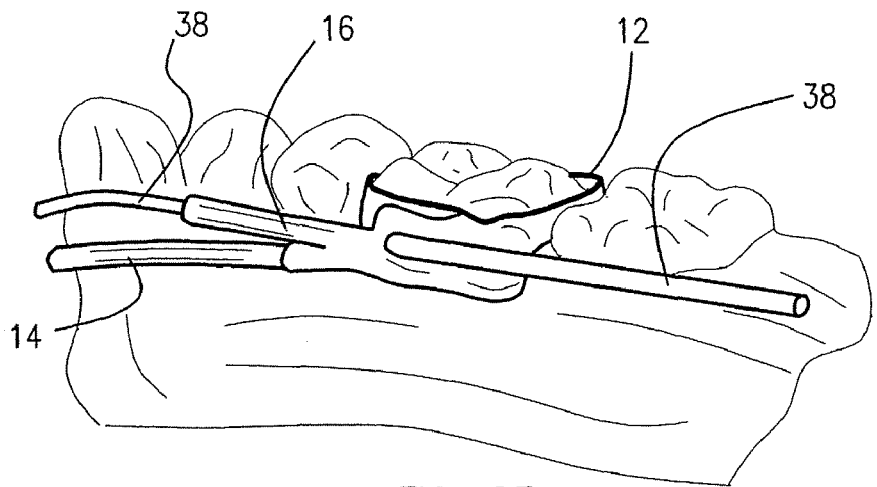

Next, the bands 12 and framework are removed from the model as shown in FIG. 23 and the removable lingual and labial components are disassembled. The soldered parts are cleaned ultrasonically. The metal parts are smoothed with heatless stone and rubber wheel. The distal ends of the lingual tubes 16 are tapered to provide better patient comfort.

Figure 24:
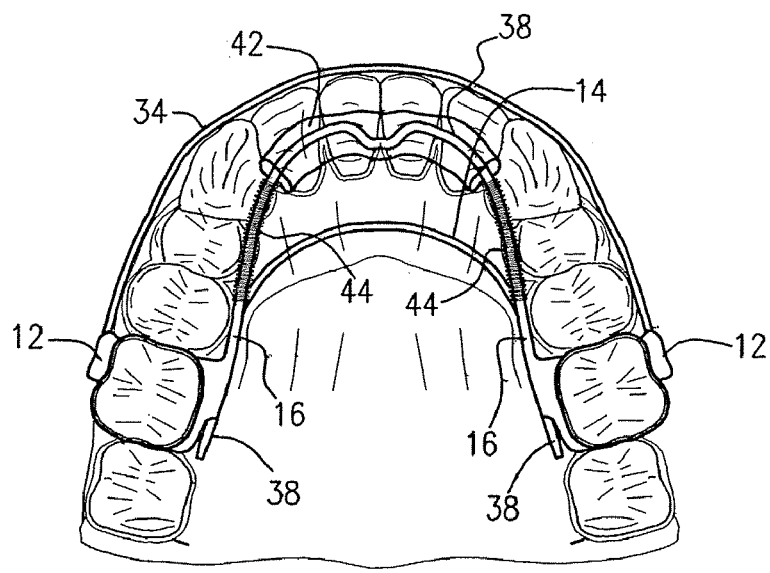

Finally, the spring-loaded biasing means are provided on the lingual and labial frames or components. In particular, the lingual component 38 is loaded with a pair of 0.010×0.030 inch NiTi open coil springs 44. For each spring, there is added about 3-4 mm. more coil length than the measured distance between the anterior end of the lingual tube and the acrylic pad of the lingual component. The appliance is placed on the duplicate of the original model to verify coil compression, and any needed adjustment is made. The appliance is returned to the setup model as shown in FIG. 24 and the distal end of the lingual wire 38 is looped 2-3 mm. behind each tube 16 toward the gingival margin.

Figure 25A:
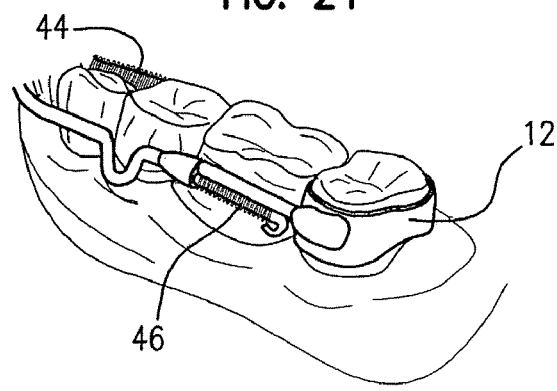
Figure 25B:
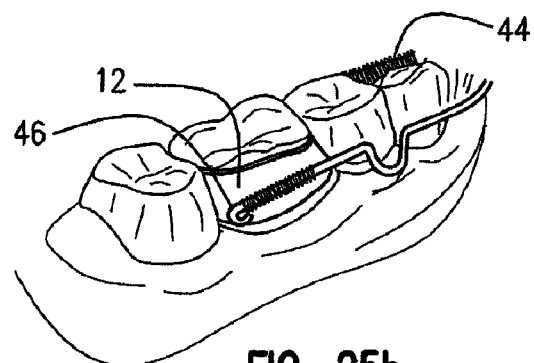

FIGS. 25a and 25b show the addition of 0.010×0.030 inch NiTi open coil springs 46, each 10-12 mm. in length, to the labial bar behind each buccal tube. A small helix stop is incorporated to the wire behind each open coil, slightly compressing it 1-2 mm. The labial component is checked to make sure it has an even pull and snaps back properly on the setup model, any necessary adjustments being made.

Figure 26:
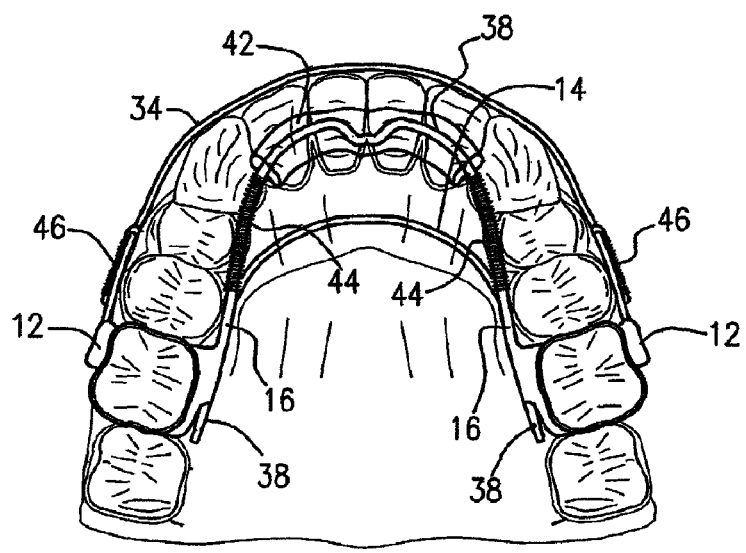
Figure 27:
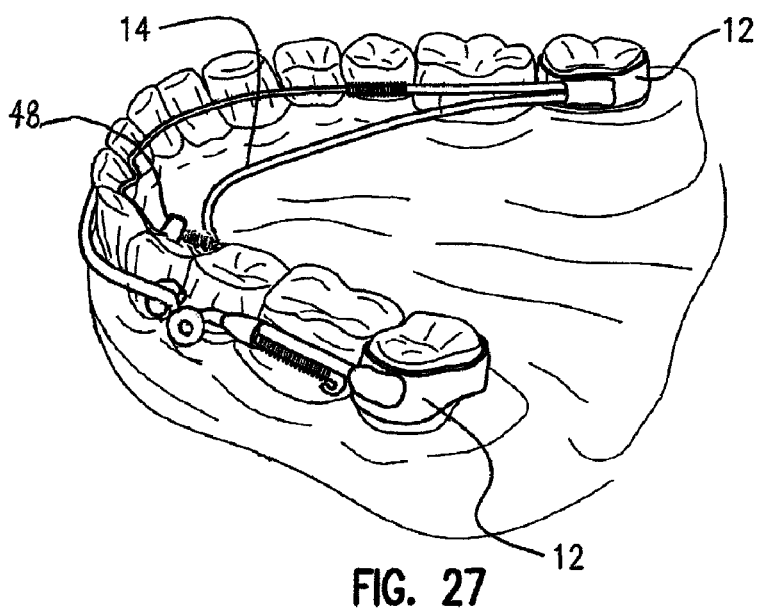

FIG. 26 shows the completed appliance installed on a maloccluded model. The labial and lingual components are checked to make sure they can travel to engage maloccluded anterior teeth. FIG. 27 shows the provision of a Gurin lock 48 or crimpable stop which may be used to recompress the open coil if needed.

Figure 28:
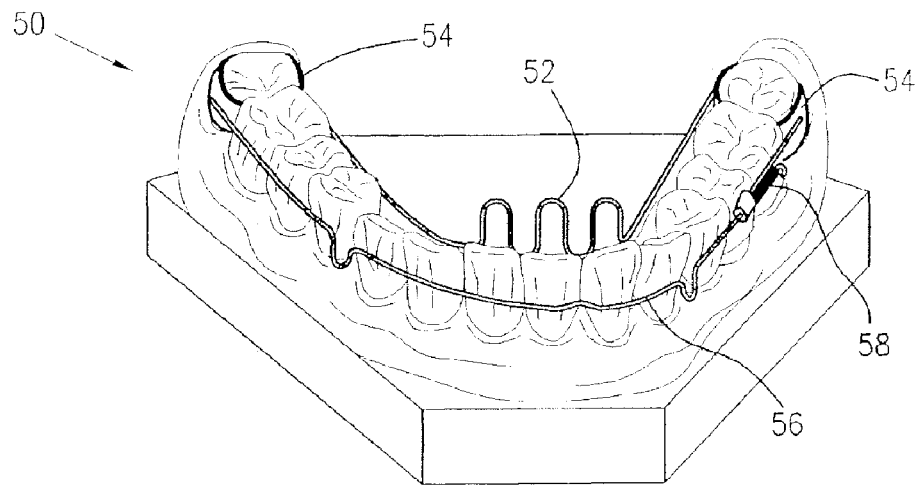
FIG. 28 is a perspective view of a habit orthodontic appliance according to this invention.

A habit orthodontic appliance 50 according to this invention is shown in FIG. 28. It is used to close anterior spacing as a finger or tongue habit is broken. The labial or outside wire is loaded with coil spring means in a manner similar to that of the appliance of U.S. Pat. No. 6,435,871 to gently pull the teeth into ideal position. The appliance can incorporate a habit-discouraging structure or component in the form of rakes, cribs or rollers, to mention a few, and is banded or fixed. In the illustrative appliance 50 of FIG. 28, a habit-discouraging structure in the form of tongue crib 52 extends between molar bands 54 and labial wire 56 is provided with coil spring biasing means, one of which is shown at 58 in FIG. 28. A labial body of acrylic material or the equivalent and provided with tooth-contacting surfaces (not shown in FIG. 28) is associated with labial frame or wire 56 in a manner similar to that of the appliance of FIG. 28.

Figure 29:
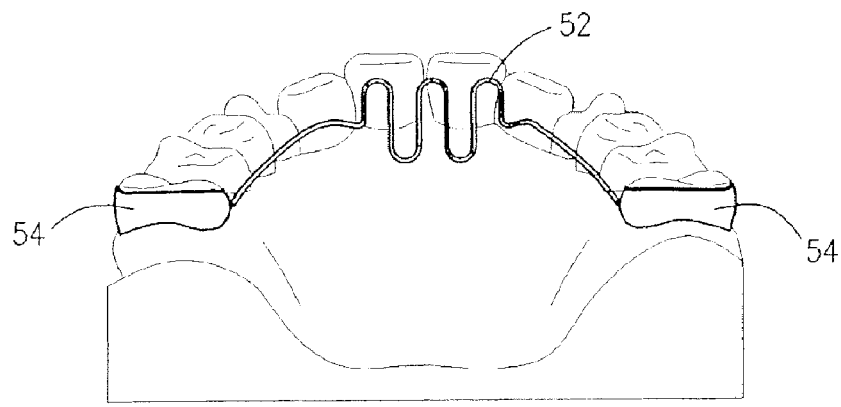
FIGS. 29-43 are perspective views illustrating a method of fabricating the appliance of FIG. 28.
Figure 30:
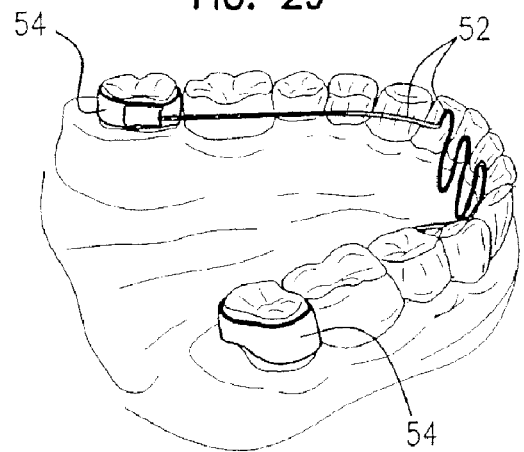
Figure 31:
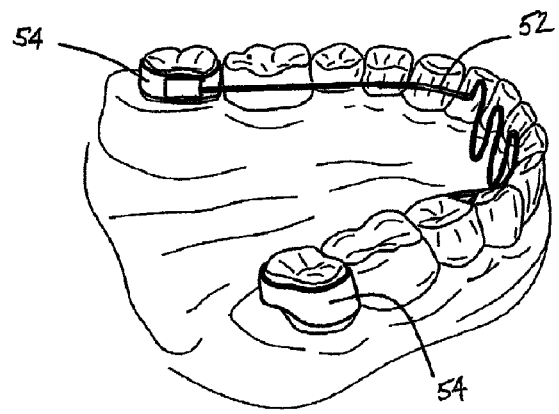

A method of fabricating appliance 50 of FIG. 28 is shown in FIGS. 29-43. FIGS. 29-31 illustrate bending of a 0.036 inch diameter DURALOY wire tongue crib 52 which is joined at each end of a molar band 54. If an optional Nance button is employed, as will be shown subsequently, the base of the crib framework extends to the middle of the rugae to support the acrylic Nance button. The crib screen can be fabricated using standard GLO Habit Crib procedures, where the crib screen is soldered to the lingual body wire.

Figure 32:
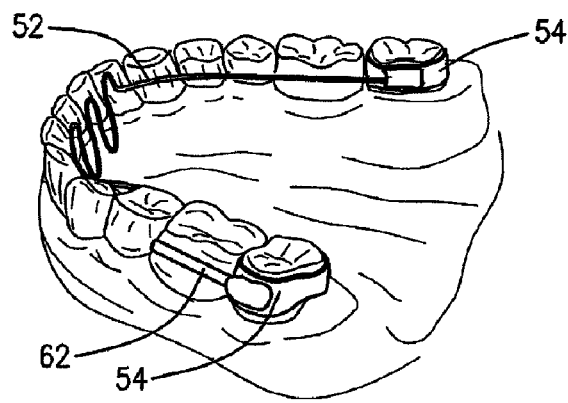
Figure 33:
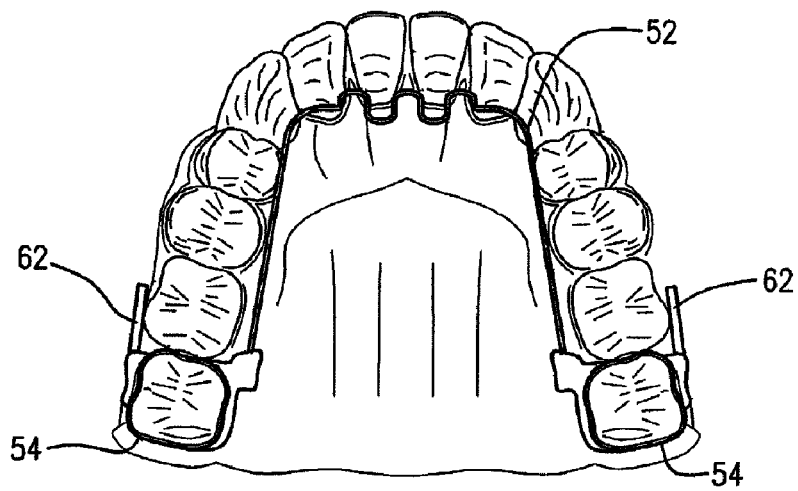

A high percentage of cases requiring the habit appliance 50 will have the bands 54 placed on the first permanent molars (6's), without the eruption of second permanent molars (7's). Thus, use of cantilever tube extensions is standard, unless second molars are exposed. As shown in FIGS. 32 and 33, 0.036 inch diameter DURALOY wire cantilever tube extensions 62 are tackwelded and soldered on the mesial-buccal, mid-height of the molar bands 54. Each wire 62 is cut near the first bicuspid/primary first molar.

Figure 34:
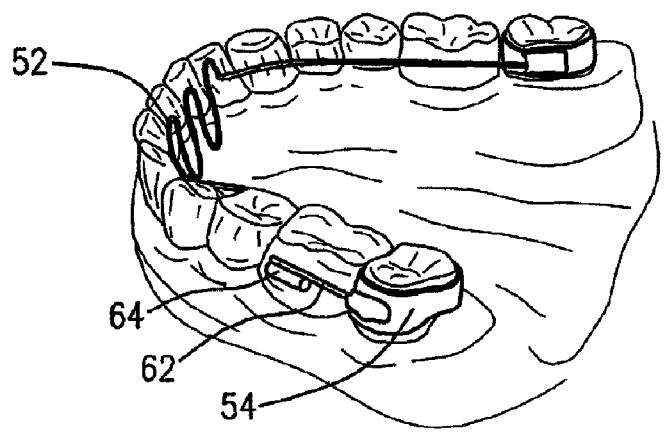
Figure 35:
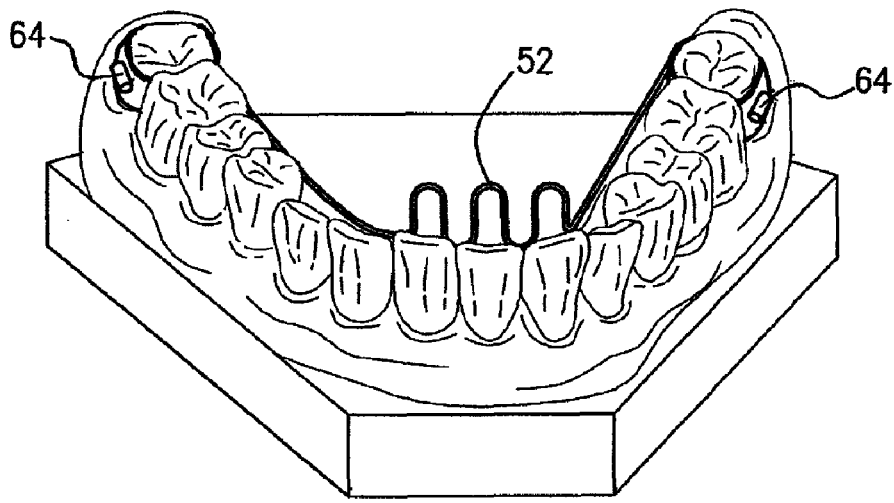
Figure 36:
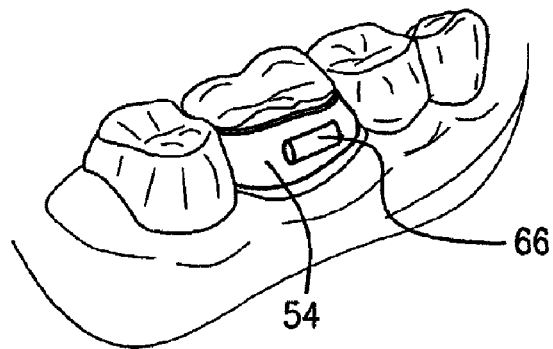

A 0.040 stainless steel tube 64 is tackwelded and soldered to the gingival side of the anterior end of each cantilever extension 62 as shown in FIGS. 34 and 35. When the second molars (7's) are exposed, facial tubes 66 are soldered directly to the mesial half of each band 54 as shown in FIG. 36. In either case, the tubes should be aligned with the dental arch form and extend as parallel with each other as possible.

Figure 37:
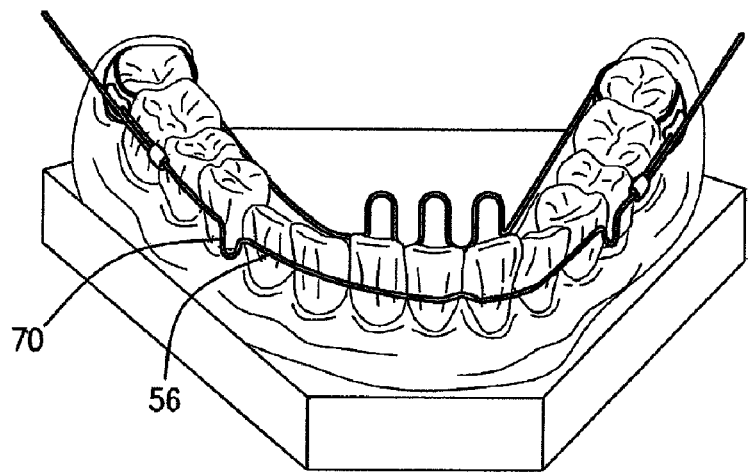
Figure 38:
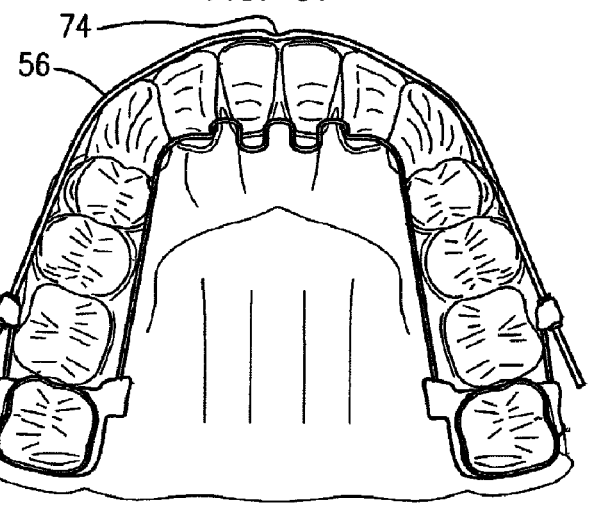
Figure 39:
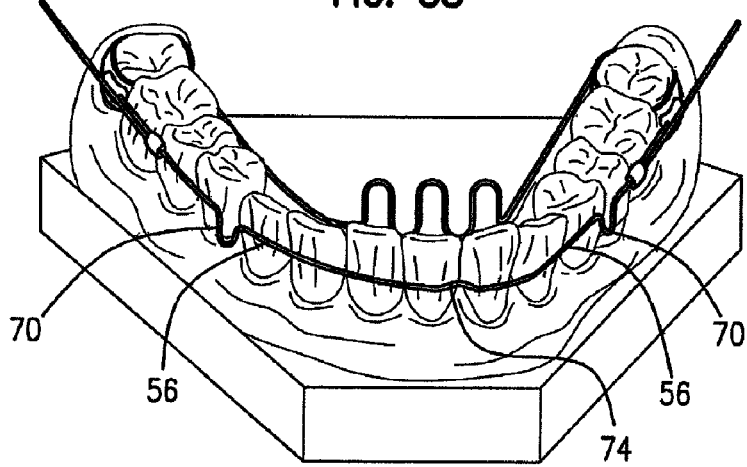

FIGS. 37-39 illustrate installation of the labial bow wire 56. In particular, a 0.028 inch diameter yellow DURALOY wire is bent to extend through each of the buccal tubes 64 or 66. A 5-7 mm. long adjustment loop 70 is placed at the mesial third of cuspids. The distal band from each adjustment loop 70 to the to the corresponding buccal tube should be more than 5 mm. in length. A V-shaped bend 74 is incorporated in the labial wire 56 at the dental midline to prevent asymmetrical retraction of the bow by the spring biasing means.

Figure 40:
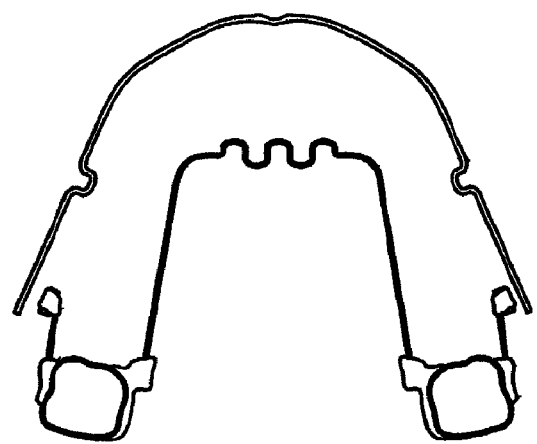

The framework is smoothed and polished as illustrated in FIG. 40. The bands and framework are removed and the removable labial component is disassembled. The soldered parts are cleaned ultrasonically. The metal parts are cleaned with heatless stone and rubber wheel.

Figure 41:
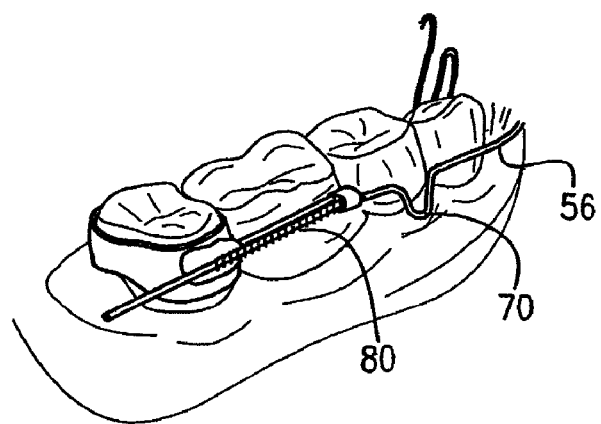
Figure 42:
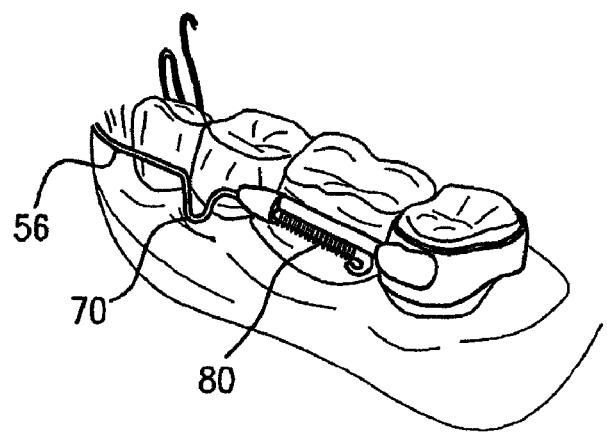

FIGS. 41 and 42 show the addition of a coil spring 80 to the labial bow 28 behind each buccal tube. Each spring is 0.010× 0.030 inch NiTi open coil and 10-12 mm. in length. A small hexix stop is incorporated in the labial bow wire 28 behind each open coil 80, compressing it approximately 75%. The labial component is checked, to make certain it has an even pull and snaps back into proper position on the setup model, and any necessary adjustments are made.

Figure 43:
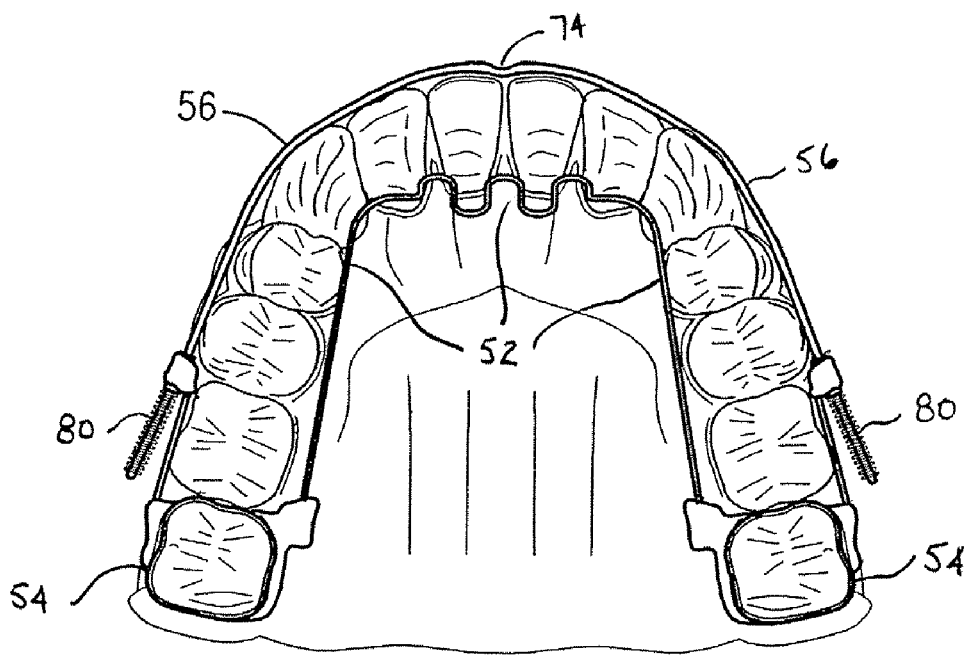
Figure 44:
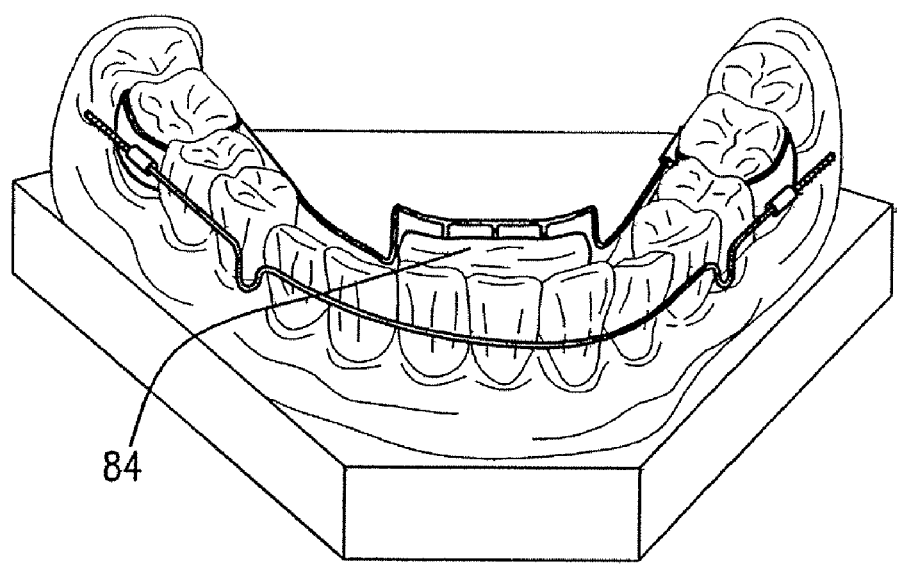
FIG. 44 is a perspective view of a habit orthodontic appliance according to another embodiment of the invention.
Figure 45:
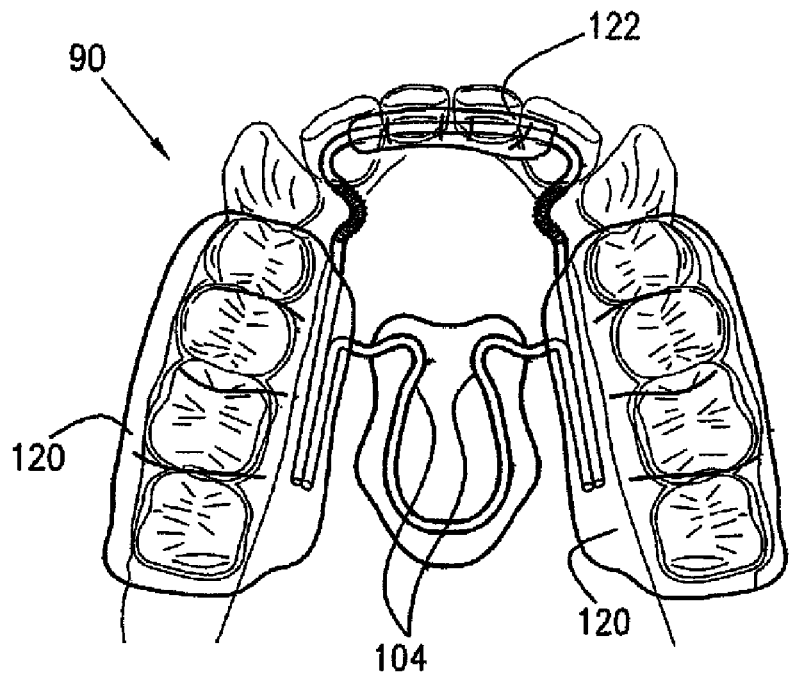
FIGS. 45-48 are perspective views of a bonded crossbite orthodontic appliance according to this invention.
Figure 46:
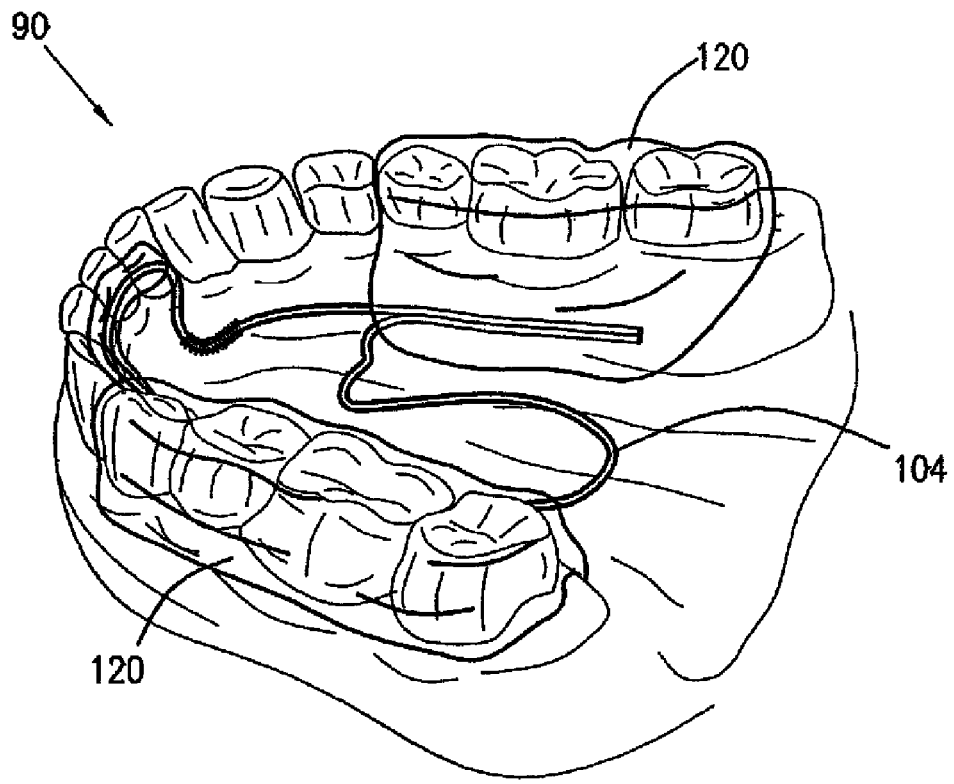
Figure 47:
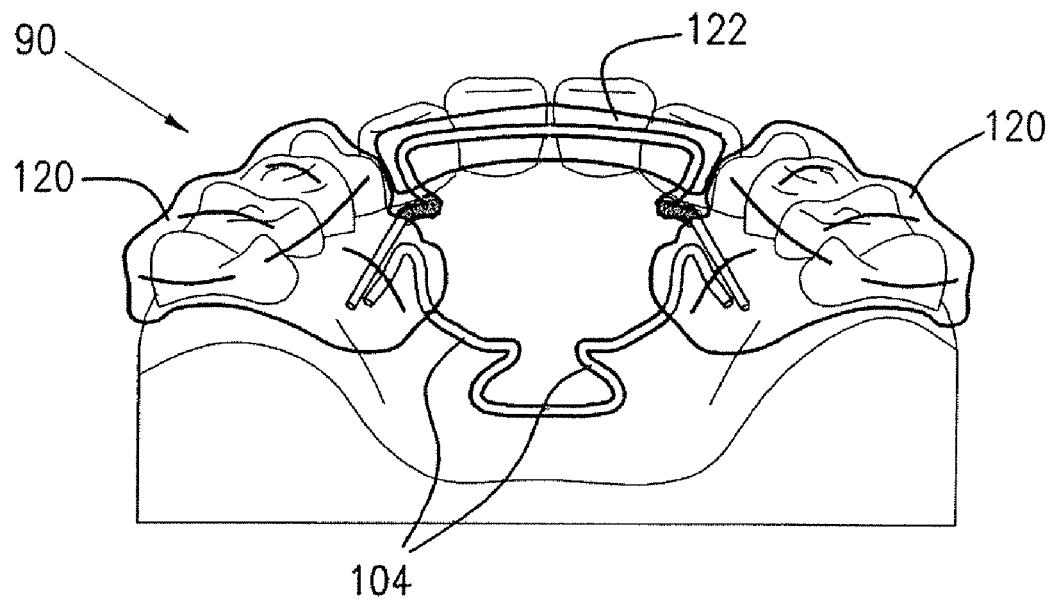
Figure 48:
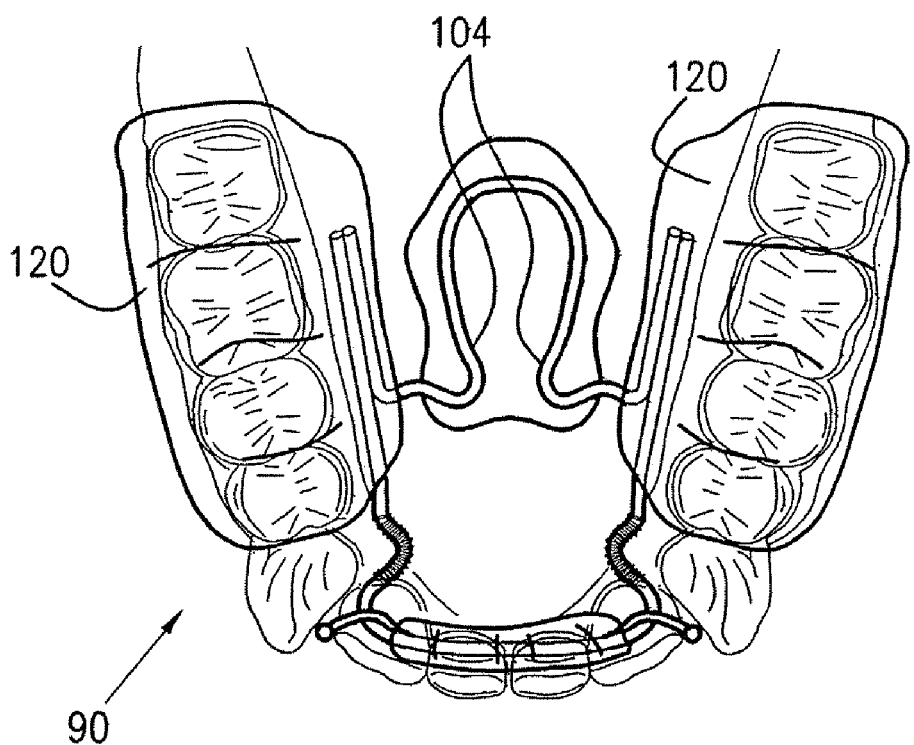

The finished appliance is shown in FIG. 43. The standard fixed habit crib, rake or roller serves as a palatal body. Normally, no teeth reset is provided. The labial coil springs close anterior spacing as the patient's habit is broken. This replaces the use of elastics and the problems associated with them riding up toward the gingival. A habit appliance with Nance Button 84 fixed to the lower portion or base of the crib screen is shown in FIG. 44.

FIGS. 45-48 illustrate a bonded crossbite orthodontic appliance 90 according to this invention. The appliance is used to gently push teeth out of anterior crossbite. The appliance is bonded in and incorporates occlusal pads to open the bite and allow the anteriors to jump or advance out of crossbite. In appliance 90 the lingual component is loaded with coil spring means in a manner similar to that of the appliance of U.S. Pat. No. 6,435,871.

Figure 49:
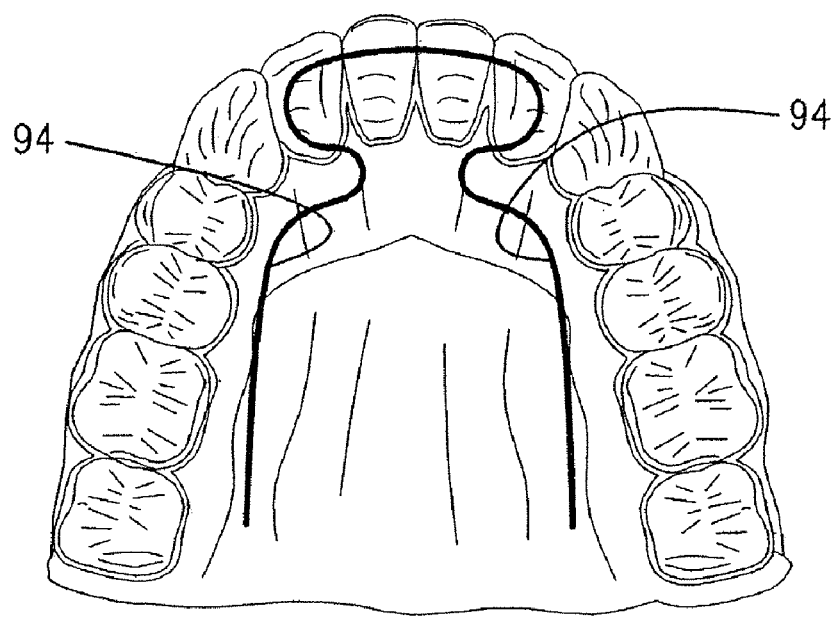
FIGS. 49-62 are perspective views illustrating a method of fabricating the appliance of FIGS. 45-48.
Figure 50:
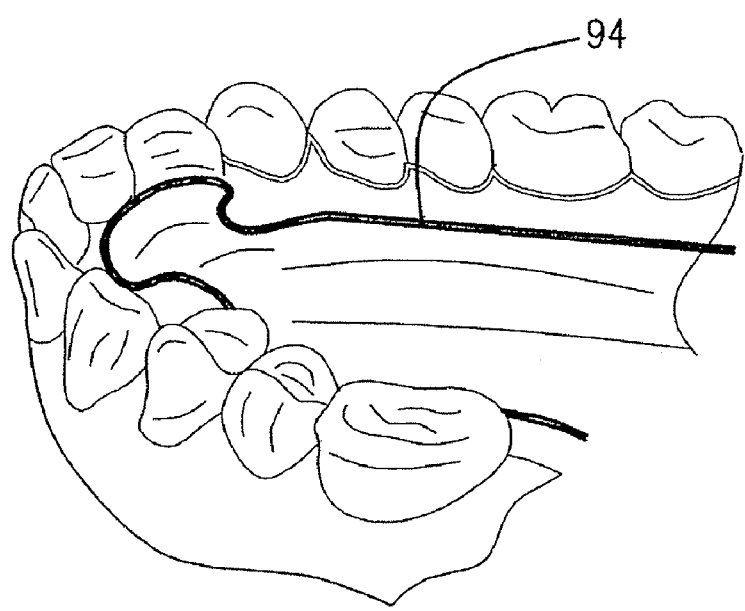
Figure 51:
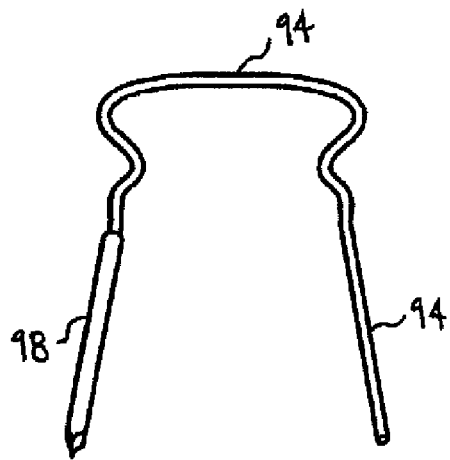
Figure 52:
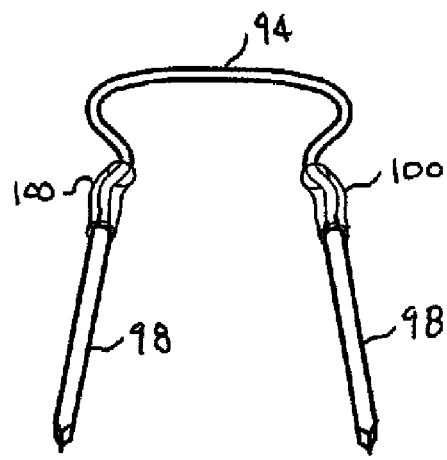

A method of fabricating appliance 90 of FIGS. 45-48 is illustrated in FIGS. 49-62. FIGS. 49 and 50 show a lingual frame or component 94 positioned in a dental model. No reset is needed, unless requested by the clinician. A 0.028 inch diameter hard spring wire DURALOY-yellow) is bent into a mushroom-shaped spring. This is done in a manner keeping the distal extensions in parallel relation. Space is allowed between the base of the spring and the model for rubber sleeves. Next, as shown in FIGS. 51 and 52, tubing is attached to lingual component 94. In particular, two lengths of 0.040 inch diameter stainless steel tubing 98 are each cut to a length from the distal of the first permanent molars to the midpoint of the first bicuspids. Plastic tubing 100 is placed on the open end of each stainless steel tube, and each tubing combination 98,100 is placed on a corresponding distal extension of lingual component 94. Each plastic tubing 100 is of a length such that it extends half-way to the wire loop of lingual component 94 as shown in FIG. 52. Each distal end of tubes 98 is crimped.

Figure 53:
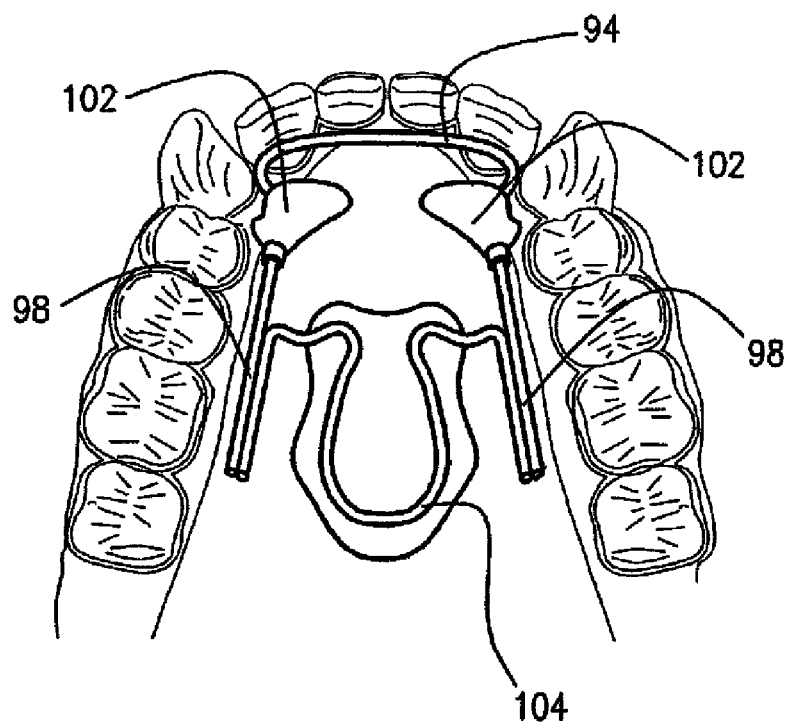
Figure 54:
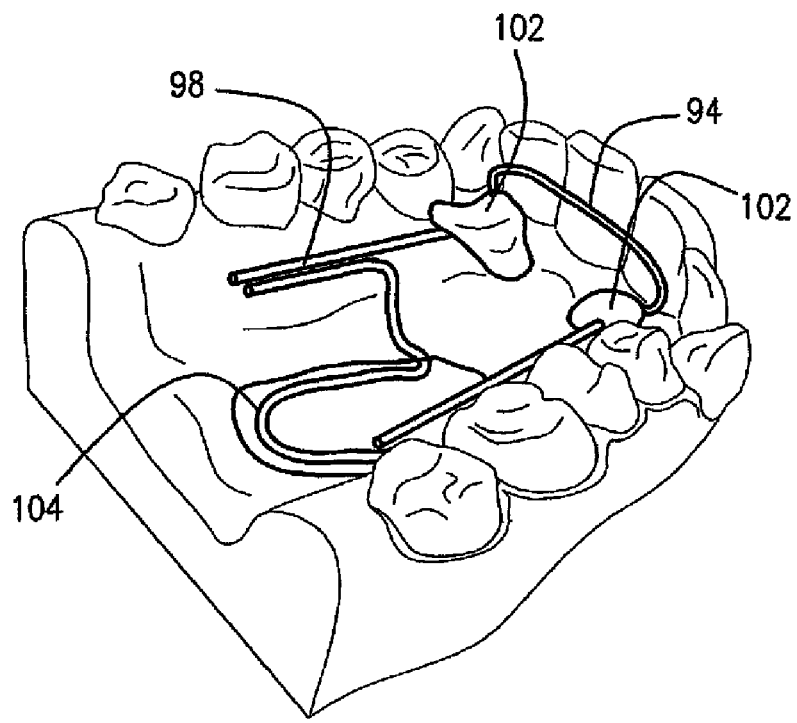

The lingual component 94 is secured in the manner illustrated in FIGS. 53 and 54. Lingual wire 94 is referenced at the interdental papilla height along the anterior teeth. Also, the steel tubes 98 are placed 1-3 mm. below the gingival margin, about 1 mm. from palatal tissue and parallel to the posterior occlusal surface. The framework is held in place with wax 102 at the loop/plastic tube area.

Figure 55:
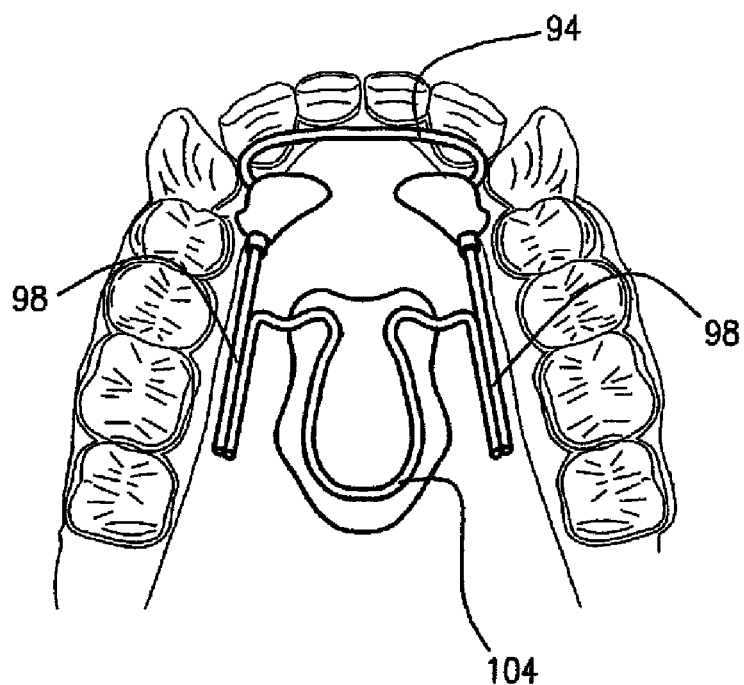
Figure 56:
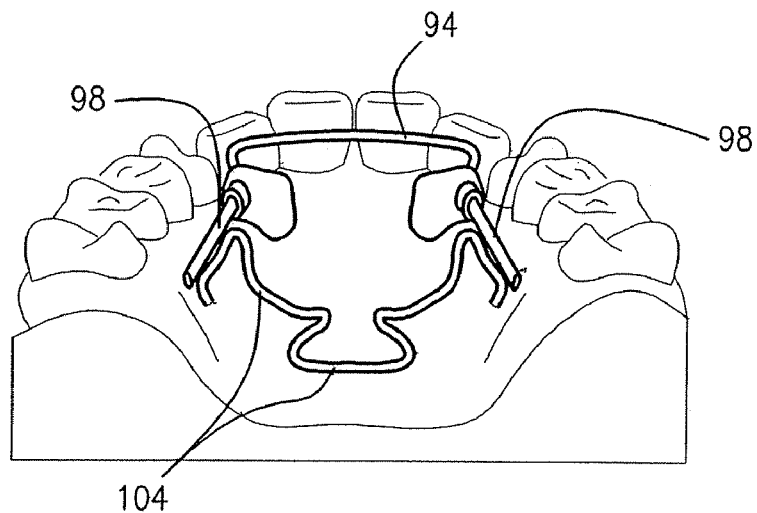

The component designated 104 in FIGS. 53 and 54 is termed a coffin wire, which is provided for improved hygiene, and is installed in the manner illustrated in FIGS. 55 and 56. A 6-7 inch length of 0.051 inch diameter stainless steel wire is formed to create an approximately 15-20 mm. long omega-shaped loop which is located about 2 mm. above the center of the palate. The anterior legs are referenced at the first and second bicuspid area and are adapted 1-2 mm. beneath the lingual component 94. An offset bend is incorporated in the wire 104, and the wire is cut near the distal of the first permanent molars.

Figure 57:
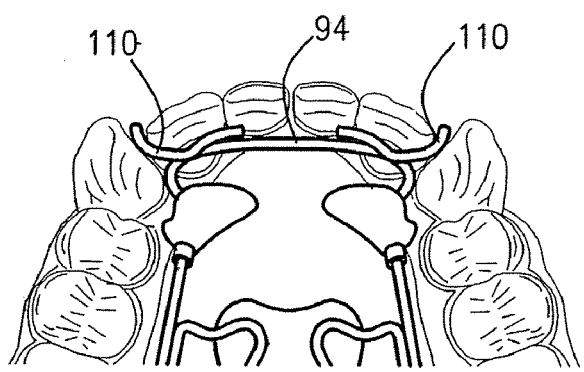
Figure 58:
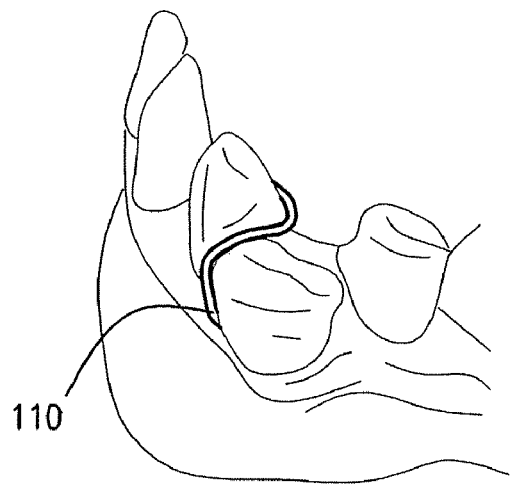

Next, ball clasp hooks are installed in the manner illustrated in FIGS. 57 and 58. This involves placing 0.028 inch diameter stainless steel ball clasps 110 distal to the lateral incisors (or cuspids). Each ball is referenced at the labial interdental papilla and is adapted tightly to follow the interdental contact. The wire of each ball clasp hook 110 is adapted to rest at the corresponding incisal edge of the lingual wire 94. An offset is placed in the end of each ball clasp hook wire to lock into acrylic which will be applied.

Appliance 90 is provided with coil springs on the arms of lingual component 94 which extend into the posterior tubes. The springs are in the form of 0.009×0.030 inch NiTi open coil springs. Enough coil should be applied to provide near-complete coil compression when placed over malocclusion.

Figure 59:
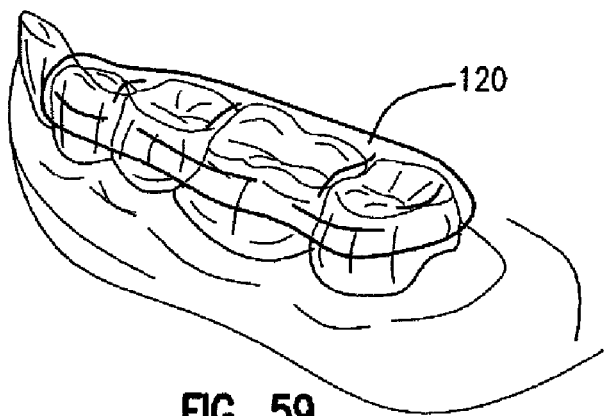
Figure 60:
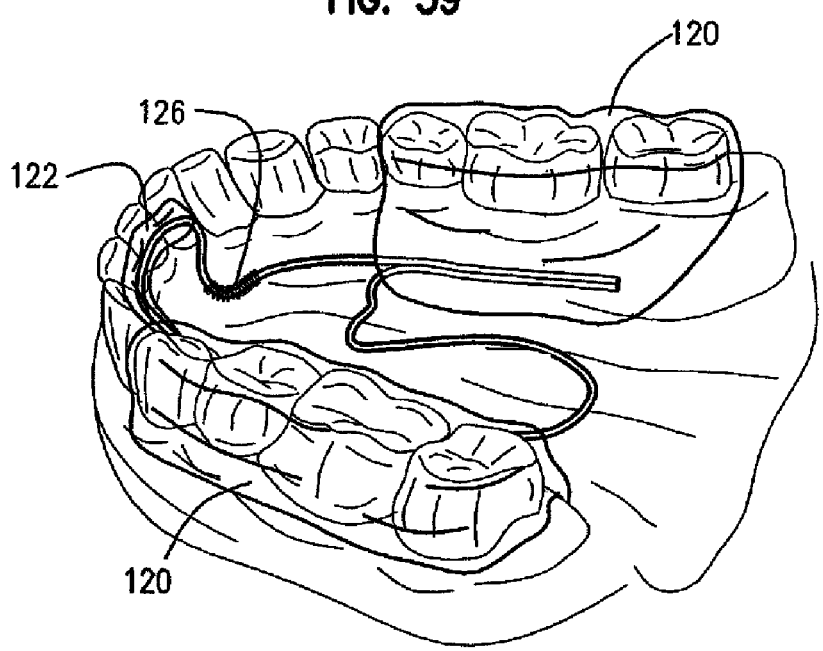
Figure 61:
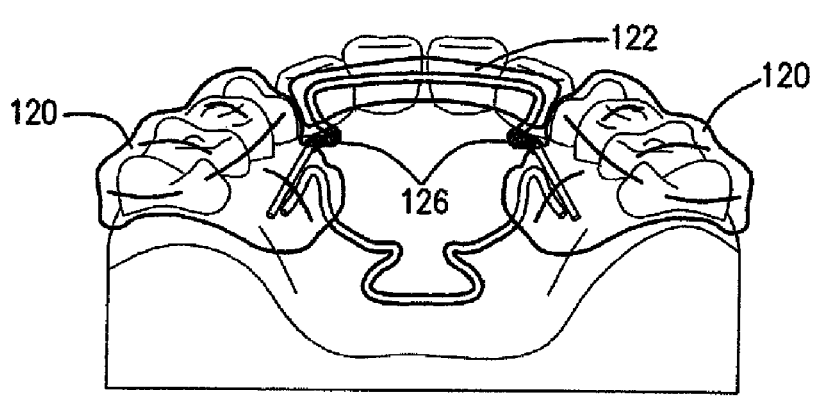

FIGS. 59-61 illustrate application of clear acrylic to the lingual component 94 (lingual of anteriors) and to form a pair of posterior bite plates or tooth-engaging portions 120. Color acrylic of choice is used to form a lingual/palatal body. By way of example, one method of forming the bite plates or tooth-engaging portions 120 can include placing a sheet of thermoplastic material over the dental model of the anterior teeth in their desired position and then placing the model with plastic sheet thereover in the receptacle of a dental appliance forming machine (not shown) such as the one commercially designated Biostar® and available from Great Lakes Orthodontics Ltd., Tonawanda, N.Y. After thermal shaping by the machine and upon cooling the material is trimmed to the desired configuration. For a more detailed description of the Biostar® machine and its method of operation, reference may be made to U.S. Pat. No. 3,768,164 issued Oct. 30, 1973 and entitled "Method of Making A Dental Appliance," the disclosure of which ip incorporated herein by reference. Each bite plate 120 is trimmed occlusally to articulate against opposing teeth. Buccal overlap is trimmed to interdental papilla height and covers the first bicuspid to the second permanent molar as shown in FIG. 59. FIG. 60 shows the acrylic 120 trimmed to a U shape into the base of the palate, approximately 10-12 mm. below the gingival margin. Referring now to FIG. 61 a thin cut is made between the anterior acrylic component 122 and the posterior bite plate 120. The acrylic is trimmed to 3-4 mm. height, centering the lingual wire in the acrylic pad 122. Acrylic is applied so as to contact all lingual teeth surfaces that are to be moved.

Figure 62:
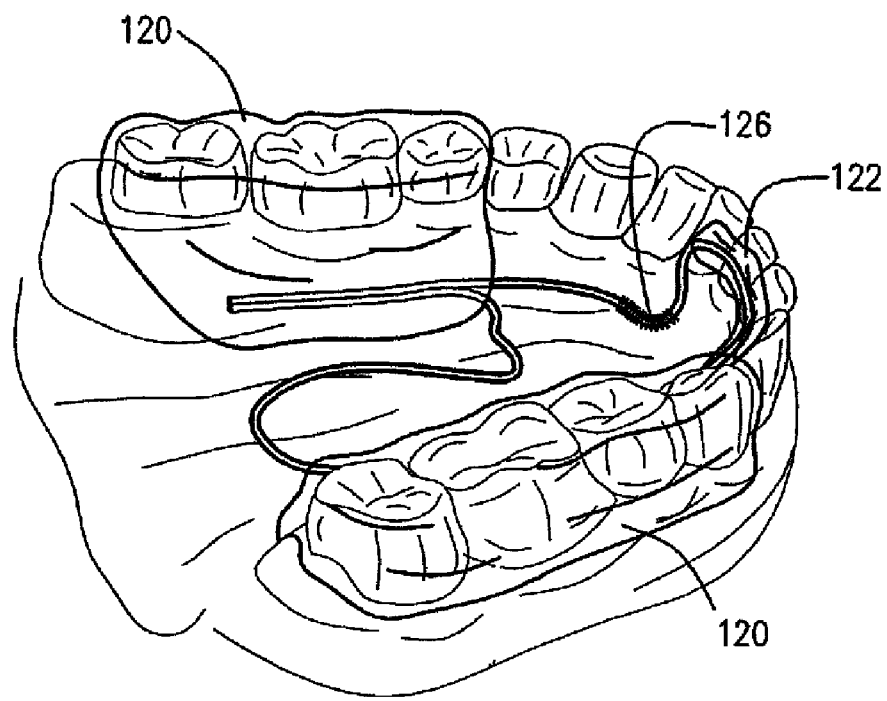

The completed appliance 90 is shown in FIG. 62. The afore-mentioned coil springs are designated 126 and shown also in FIGS. 60 and 61. They apply force between lingual body 122 and the bite plates 120. The springs together with the posterior bite plates or pads open the patient's bite and allow anteriors to jump. Mixed dentition is corrected, and appliance 90 eliminates the need for finger springs, screws and adjustments. The force is constant, and does not deflect toward the incisal, unlike finger springs.

Figure 63:
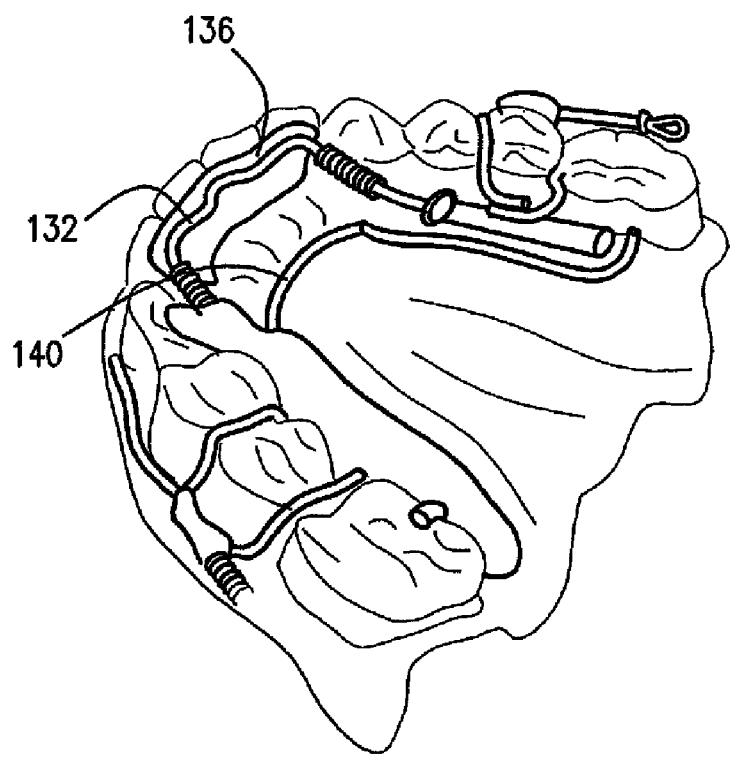
FIGS. 63-65 are perspective views of a new lingual component for use in the appliance of this invention.
Figure 64:
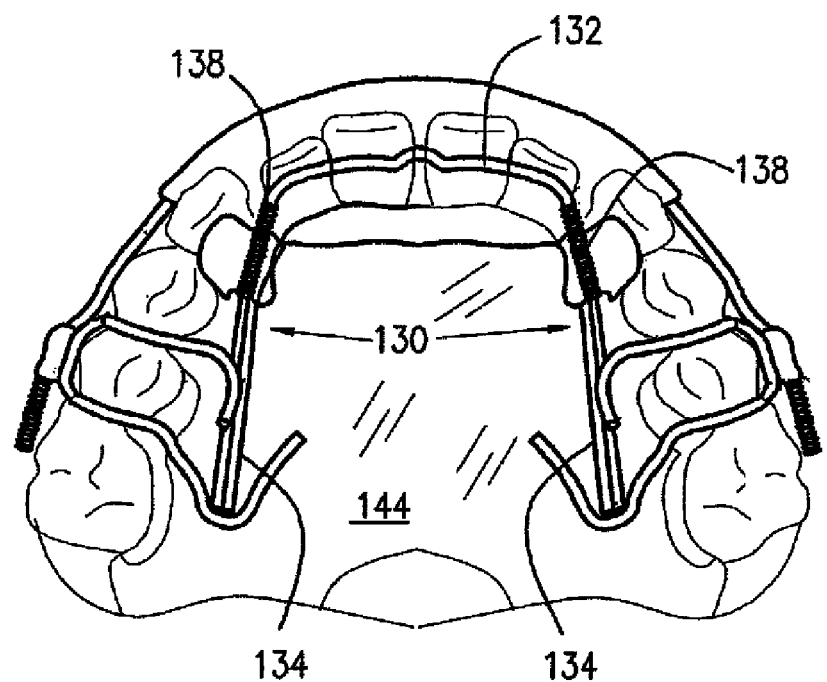
Figure 65:
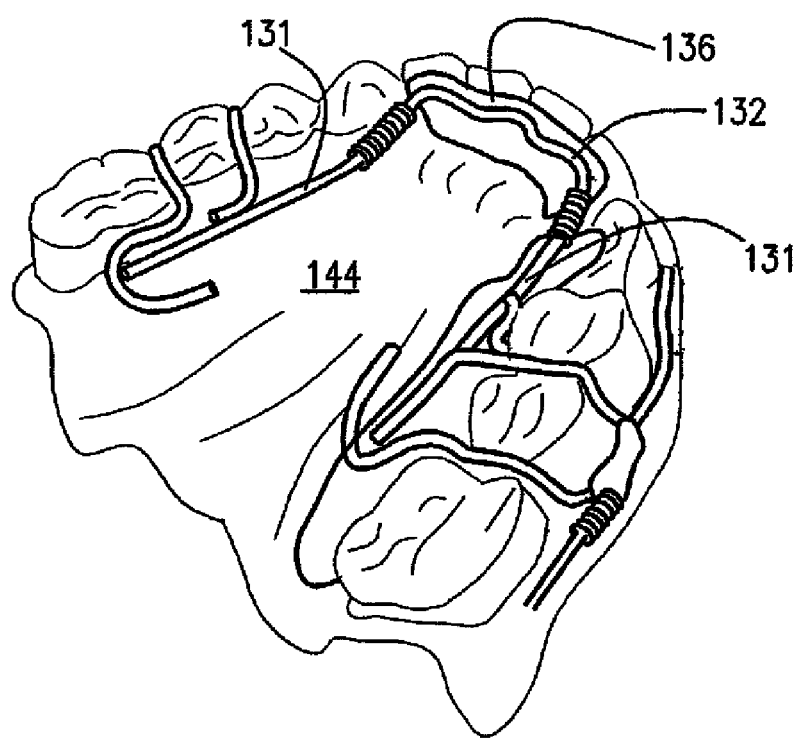

FIGS. 63-65 illustrate an alternative form of lingual component for use in orthodontic appliances of the type described herein. The labial component is similar to that of the appliance of U.S. Pat. No. 6,435,871. The lingual component 130 has an anterior portion 132 which meets posterior portions 134 at approximately right angles. Anterior portion 132 is within an acrylic body 136 and the labial component has coil spring biasing means 138. A lingual support wire 140 also is provided as shown in FIGS. 64 an 65. An acrylic palatal body 144 associated with both labial and lingual components is shown in FIGS. 64 and 65. It serves to provide anchorage for the appliance. The shape of lingual component 130 enhances patient comfort by providing a structure where there is less space for the tongue to go between anterior and posterior portions of the appliance. In addition, disposing posterior portions 134 at approximately right angles to anterior portion 132 provides a more direct route for transfer of force to the target anterior teeth.

Figure 66:
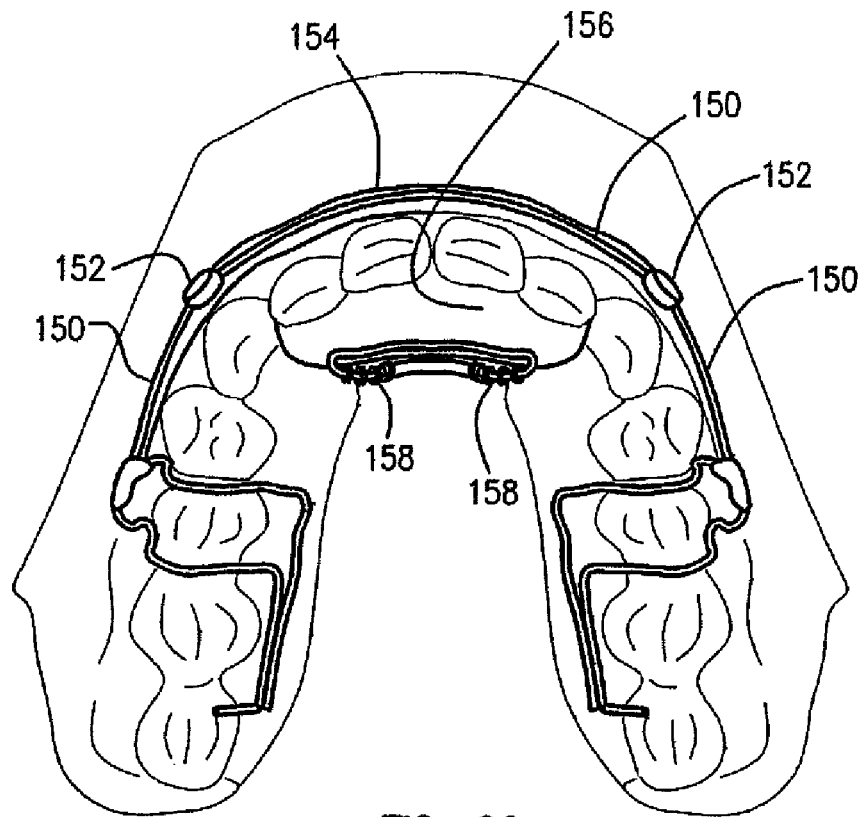
FIGS. 66 and 67 are perspective views of a new labial bow for use in the appliance of this invention.
Figure 67:
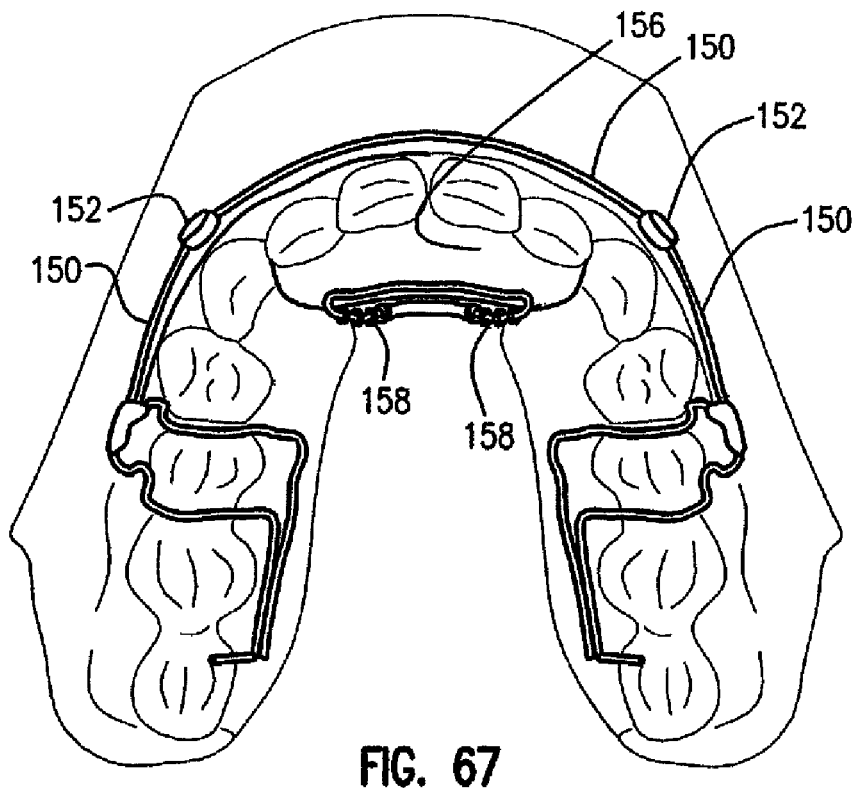

FIGS. 66 and 67 illustrate an alternative form of labial bow 150 for use in orthodontic appliances of the type described herein. Its primary function is to serve as a support for the anterior teeth while force is applied by the lingual components of the appliance. Labial bow 150 can apply some force to the anterior teeth if desired, by the provision of the loops 152 which can be adjusted to control the force applied by bow 150. A labial body 154 of acrylic or like material and having tooth-contacting surfaces is associated with labial bow 150 in a manner similar to the appliances previously described. A lingual body 156 of acrylic or like material has tooth-contacting surfaces and is operatively associated with the lingual frame and compression springs 158 in a manner similar to the appliances previously described.

Figure 68:
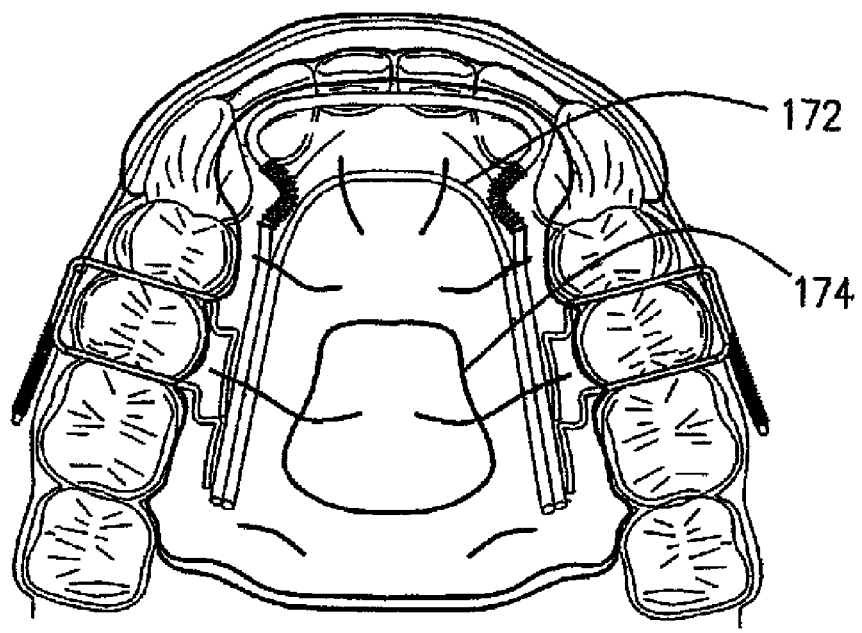
FIG. 68 is a perspective view of an alternative form of the appliance of FIGS. 63-65.
Figure 69:
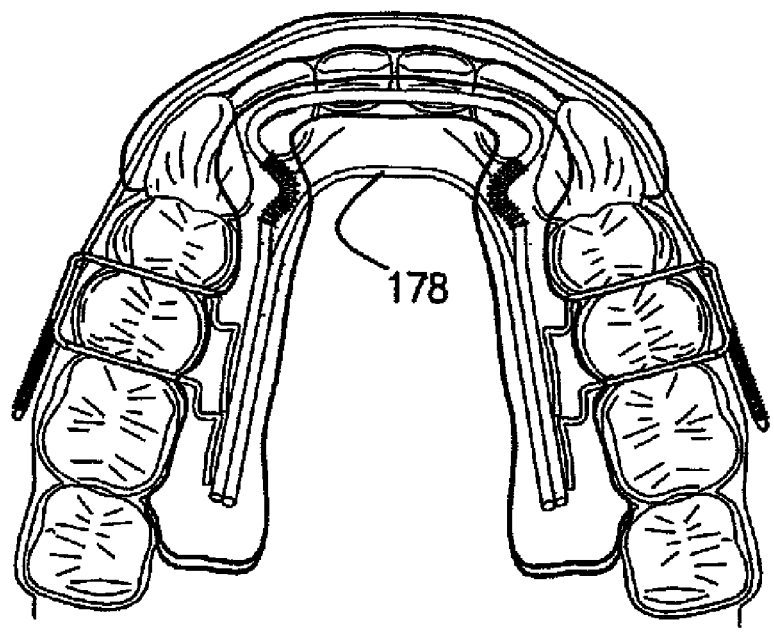
FIG. 69 is a perspective view of an alternative form of the appliance of FIG. 68.

The appliance shown in FIG. 68 is similar to the appliance of FIGS. 63-65 except that the lingual frame or wire has the mushroom shape like that in the appliance of U.S. Pat. No. 6,435,871. It includes a lingual support component 172 like wire 140 shown in FIG. 63. Whereas the appliance of FIG. 68 has a palatal support body 174, the appliance of FIG. 69 uses a lingual support wire 178 having a diameter of about 0.051 inch to give the appliance strength and function without palatal acrylic.

While embodiments of the invention have been described in detail, that has been done for the purpose of illustration, not limitation.

The invention claimed is:

1. An orthodontic appliance for treatment of one or more anterior teeth in a jaw of a patient comprising:
   a pair of bands adapted to be secured to posterior teeth spaced from the anterior teeth;
   a labial body having teeth-contacting surfaces for engaging the labial side of the anterior teeth;
   a labial frame operatively connected between the labial body and the pair of bands;
   a lingual body having teeth-contacting surfaces for engaging the lingual side of the anterior teeth, wherein the labial body is configured to span more than one anterior tooth and the labial body is configured to not be fixedly attached to the labial side of the anterior teeth;
   a lingual frame operatively connected between the lingual body and the pair of bands;
   spring-loaded biasing means on the labial and lingual frames for causing the labial and lingual bodies to apply corrective forces to the anterior teeth; and
   a lingual support component connected to the pair of bands and extending toward the anterior teeth.

2. The orthodontic appliance according to claim 1, wherein the lingual support component is in the general shape of a U having two ends and a pad, with the ends attached to the bands and the web pad located near the anterior teeth.

3. The orthodontic appliance according to claim 1, wherein the lingual support component comprises a generally U-shaped wire having two ends thereof attached to the bands and extending toward the anterior teeth.

4. The orthodontic appliance according to claim 2, wherein the pad of the lingual support component is located below the gingival margin along the exterior teeth.

5. The orthodontic appliance according to claim 3, wherein the lingual support component extends toward a location below the gingival margin along the anterior teeth.

6. A method of making an orthodontic appliance for treatment of one or more anterior teeth in a jaw of a patient comprising:
   providing a model of a dental arch of a patient wherein the anterior teeth are in desired locations;
   installing a pair of bands on oppositely-located model teeth spaced posteriorly from the model anterior teeth;
   mounting a tubular component on the lingual side of each band and orienting the open end of each tube toward the anterior teeth;
   providing a lingual support component in the form of a generally U-shaped wire and attaching the ends of the component to the lingual sides of the bands;
   mounting a tubular component on the buccal side of each band and orienting the open end of each tube toward the anterior portion of the jaw;
   providing a labial frame component in the form of a generally U-shaped wire and inserting the ends of the wire through the tubular components on the buccal sides of the bands;
   providing a lingual frame component in the form of a generally U-shaped wire and inserting the ends of the wire through the tubular components on the lingual sides of the bands;

providing a labial support body on the labial frame component, the labial support body having teeth-contacting surfaces for engaging the labial side of the anterior teeth;

providing a lingual support body on the lingual frame component, the lingual support body having teeth-contacting surfaces for engaging the lingual side of the anterior teeth;

installing spring-loaded biasing means on the lingual frame component between the lingual support body and the tubular components on the lingual sides of the bands; and installing spring-loaded biasing means on the labial frame component between the tubular components on the buccal sides of the bands and the ends of the labial frame component.

7. The method according to claim 6, further including positioning the lingual support component to extend toward the anterior teeth.

8. The method according to claim 6, further including positioning the lingual support component to extend toward a location below the gingival margin along the anterior teeth.

9. The method according to claim 6, further including disposing the tubular support components on the buccal and lingual sides of each band to be substantially mutually parallel and in substantial alignment with the dental arch.

10. An orthodontic appliance for treatment of one or more anterior teeth in a jaw of a patient comprising:
 a pair of attachments adapted to be secured to posterior teeth spaced from the anterior teeth;
 a labial body having teeth-contacting surfaces for engaging the labial side of the anterior teeth, wherein the labial body is configured to span more than one anterior tooth and the labial body is configured to not be fixedly attached to the labial side of the anterior teeth;
 a labial frame operatively connected between the labial body and the pair of attachments;
 a lingual body having teeth-contacting surfaces for engaging the lingual side of the anterior teeth;
 a lingual frame operatively connected between the lingual body and the pair of attachments, the lingual frame having an anterior portion which meets posterior portions at substantially right angles;
 spring-loaded biasing means on the labial and lingual frames for causing the labial and lingual bodies to apply corrective forces to the anterior teeth; and
 a lingual support component connected to the pair of attachments and extending toward the anterior teeth.

11. The orthodontic appliance according to claim 10, further including a palatal body associated with the labial and lingual frames for anchoring the appliance.

12. An orthodontic appliance for treatment of one or more anterior teeth in a jaw of a patient comprising:
 a pair of attachments adapted to be secured to posterior teeth spaced from the anterior teeth;
 a labial body having teeth-contacting surfaces for engaging the labial side of the anterior teeth, wherein the labial body is configured to span more than one anterior tooth and the labial body is configured to not be fixedly attached to the labial side of the anterior teeth;
 a labial frame operatively connected between the labial body and the pair of attachments;
 a lingual body having teeth-contacting surfaces for engaging the lingual side of the anterior teeth;
 a lingual frame operatively connected between the lingual body and the pair of attachments;
 spring-loaded biasing means on the lingual frame for causing the lingual body to apply corrective forces to the anterior teeth; and
 the labial frame and body serving to support the anterior teeth during application of corrective forces thereto.

13. The orthodontic appliance according to claim 12, further including a lingual support component connected to the pair of attachments and extending toward the anterior teeth.

14. The orthodontic appliance according to claim 12, further including at least one adjustment formation in the labial frame to enable some force to be applied to the anterior teeth by the labial frame and labial body.

* * * * *